United States Patent
McGonigle

(10) Patent No.: US 9,719,102 B2
(45) Date of Patent: Aug. 1, 2017

(54) METHODS AND COMPOSITIONS FOR SILENCING GENE FAMILIES USING ARTIFICIAL MICRORNAS

(71) Applicant: E I DU PONT DE NEMOURS AND COMPANY, Wilmington, DE (US)

(72) Inventor: Brian McGonigle, Wilmington, DE (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 106 days.

(21) Appl. No.: 14/716,955

(22) Filed: May 20, 2015

(65) Prior Publication Data

US 2015/0252376 A1     Sep. 10, 2015

Related U.S. Application Data

(62) Division of application No. 13/462,922, filed on May 3, 2012, now Pat. No. 9,062,317.

(60) Provisional application No. 61/484,033, filed on May 9, 2011.

(51) Int. Cl.
    *C12N 15/82*      (2006.01)

(52) U.S. Cl.
    CPC ..... *C12N 15/8218* (2013.01); *C12N 15/8245* (2013.01); *C12N 15/8247* (2013.01)

(58) Field of Classification Search
None
See application file for complete search history.

(56) References Cited

U.S. PATENT DOCUMENTS

2009/0155910 A1*   6/2009   McGonigle ........ C12N 15/8216 435/419

FOREIGN PATENT DOCUMENTS

| WO | 2009/079532 | 6/2009 |
|----|-------------|--------|
| WO | 2009/079548 | 6/2009 |

OTHER PUBLICATIONS

Cuperus et al, 2010, Nat. Structural & Mol. Bio., 17:997-1004.*
Ho-Ming Chen et al., 22-nucleotide RNAs trigger secondary siRNA biogenesis inplants, PNAS, Aug. 24, 2010, vol. 107, No. 34, pp. 15269-15274.
Josh T. Cuperus et al., Unique functionality of 22-nt miRNAs in triggering RDR6-dependent siRNA biogenesis from target transcripts in Arabidopsis, Nature Structural & Molecular Biology, Aug. 2010, vol. 17, No. 8, pp. 997-1003.
XP-002682193—Supplementary Information for Unique Functionality of 22-nt miRNAs in Triggering RDR6-dependent SiRNA biogenesis from Target Transcripts.
Qi-Wen Niu et al., Expression of artificial microRNAs in transgenic Arabidopsis thaliana confers virus resistance, Nature Biotechnology, Nov. 2006, vol. 24, No. 11, pp. 1420-1428.
Rebecca Schwab et al., High Specific Gene Silencing by Artificial MicroRNAs in Arabidopsis, The Plant Cell, May 2006, vol. 18, pp. 1121-1133.
Rebecca Schwab et al, Specific Effects of MicroRNAs on the Plant Transcriptome, Development Cell, Apr. 2005, vol. 8, pp. 517-527.
Titia Sijen et al., On the Role of RNA Amplification in dsRNA-Triggered Gene Silencing, Cell, Nov. 16, 2001, vol. 107, pp. 465-476.
Fabian E. Valistij et al., Spreading of RNA Targeting and DNA Methylation in RNA Silencing Requires Transcriptin of the Target Gene and a Putative RNA-Dependent RNA Polymerase, The Plant Cell, Apr. 2002, vol. 14, pp. 857-867.
International Search Report PCT/US2012/037083.

* cited by examiner

*Primary Examiner* — Jason Deveau Rosen

(57) ABSTRACT

Methods and compositions are provided which allow for a single microRNA (miRNA) to reduce the level of expression of at least two members of the same protein and/or gene family. While a single 21 base pair miRNA can cause cleavage of a variety of species of mRNAs, an entire gene family cannot be silenced unless that gene family shares near identity within a 21 base pair region that is also able to be cleaved by a single miRNA. In certain embodiments, all members of a given protein and/or gene family can be suppressed with a miRNA expression construct disclosed herein even if they do not share near identity within a 21 base pair region that is also able to function as a miRNA. Such methods and compositions employ miRNA expression constructs having a structure such that the most abundant form of miRNA produced from the construct is a 22-nucleotide miRNA. The 22-nucleotide miRNA produced from the miRNA expression construct thereby reduces the level of expression of not only the target sequence for the miRNA, but also reduces the level of expression of at least one additional sequence from the same protein and/or gene family as the target sequence.

8 Claims, 5 Drawing Sheets

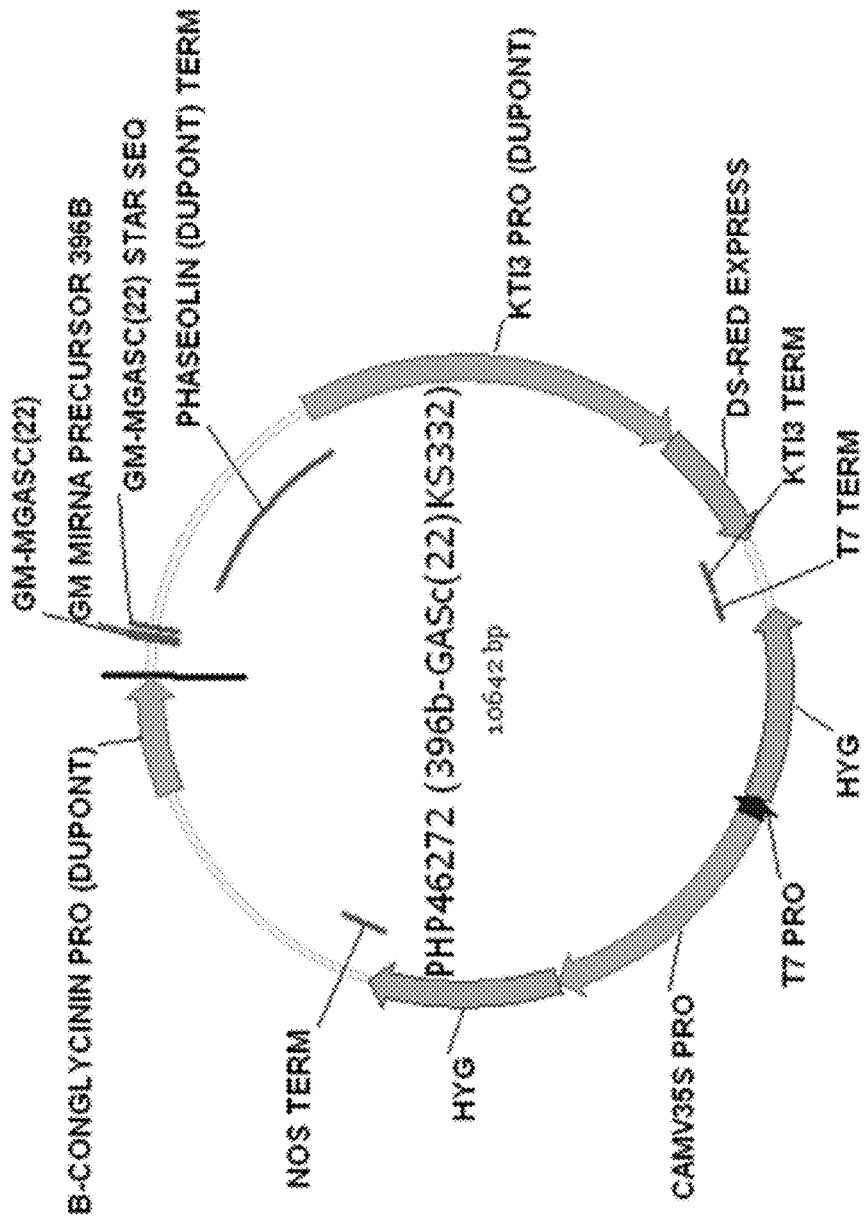
FIG. 1 PHP46272

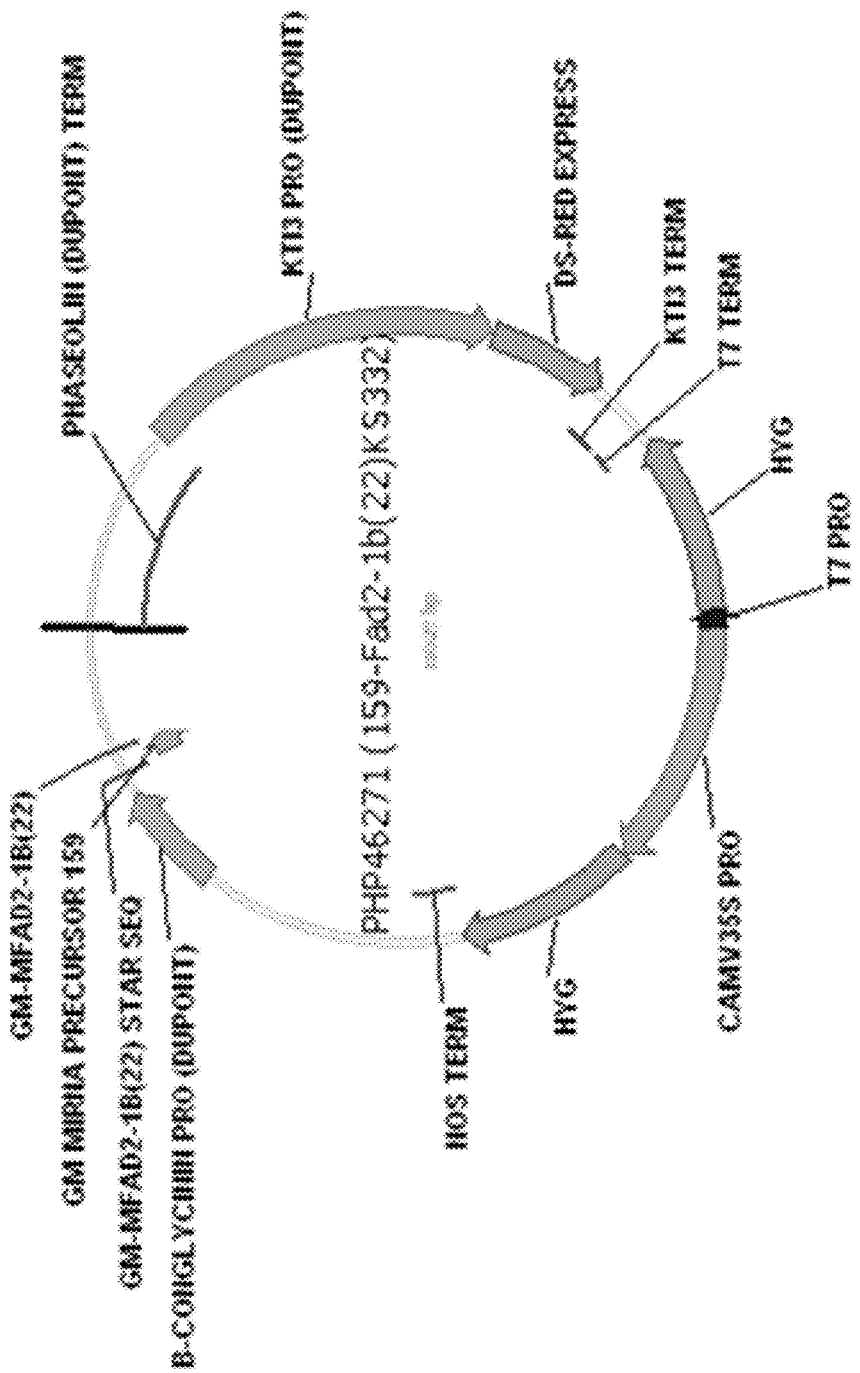
FIG. 2 PHP46271

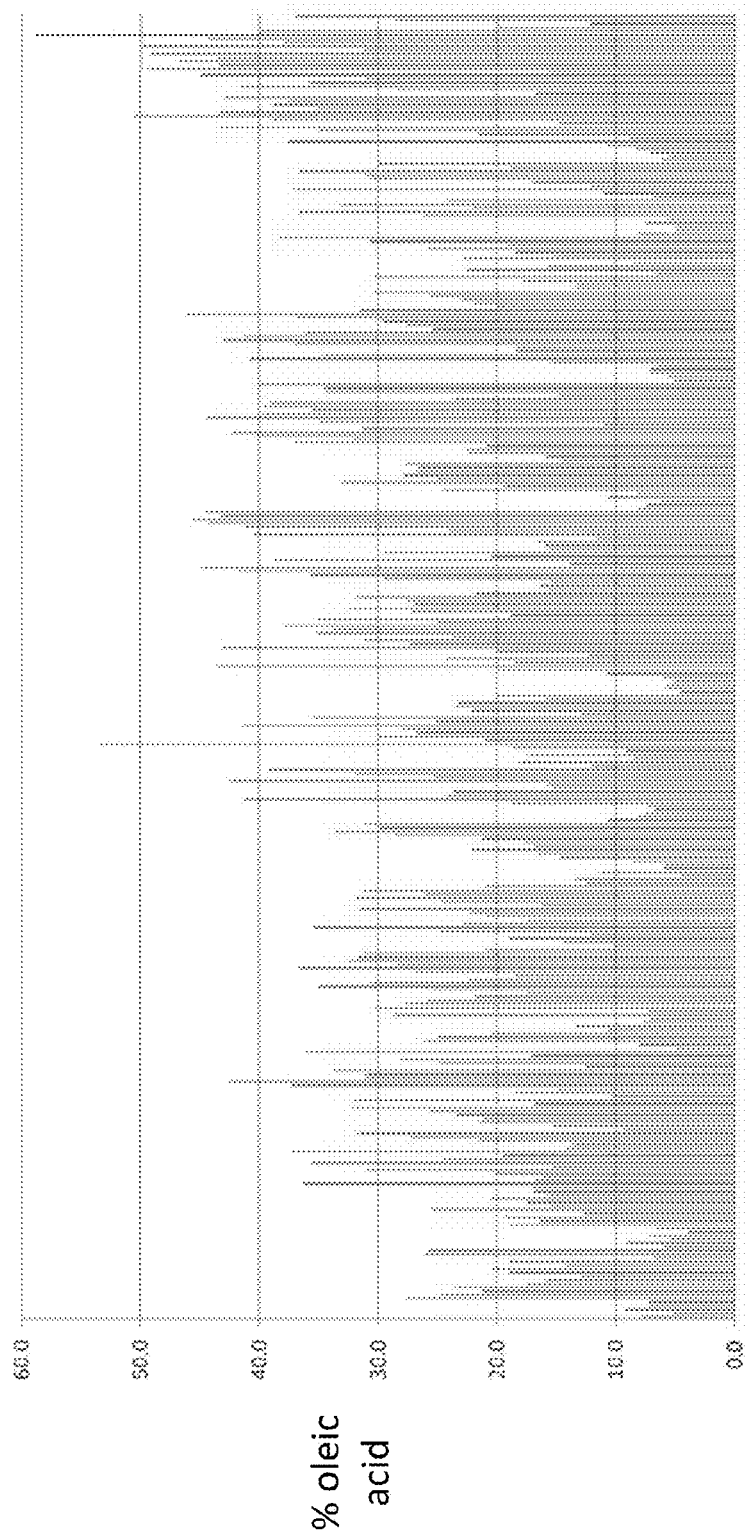

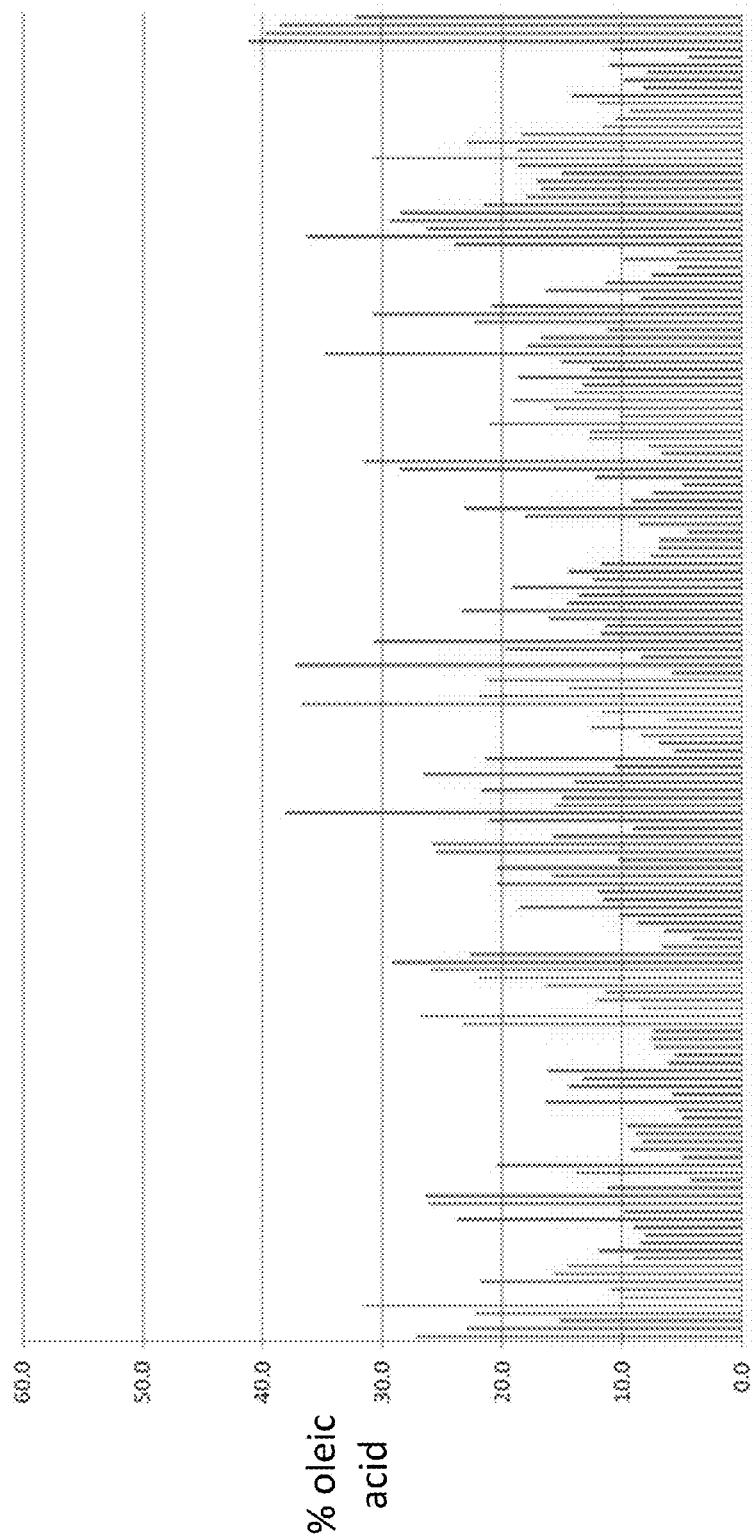

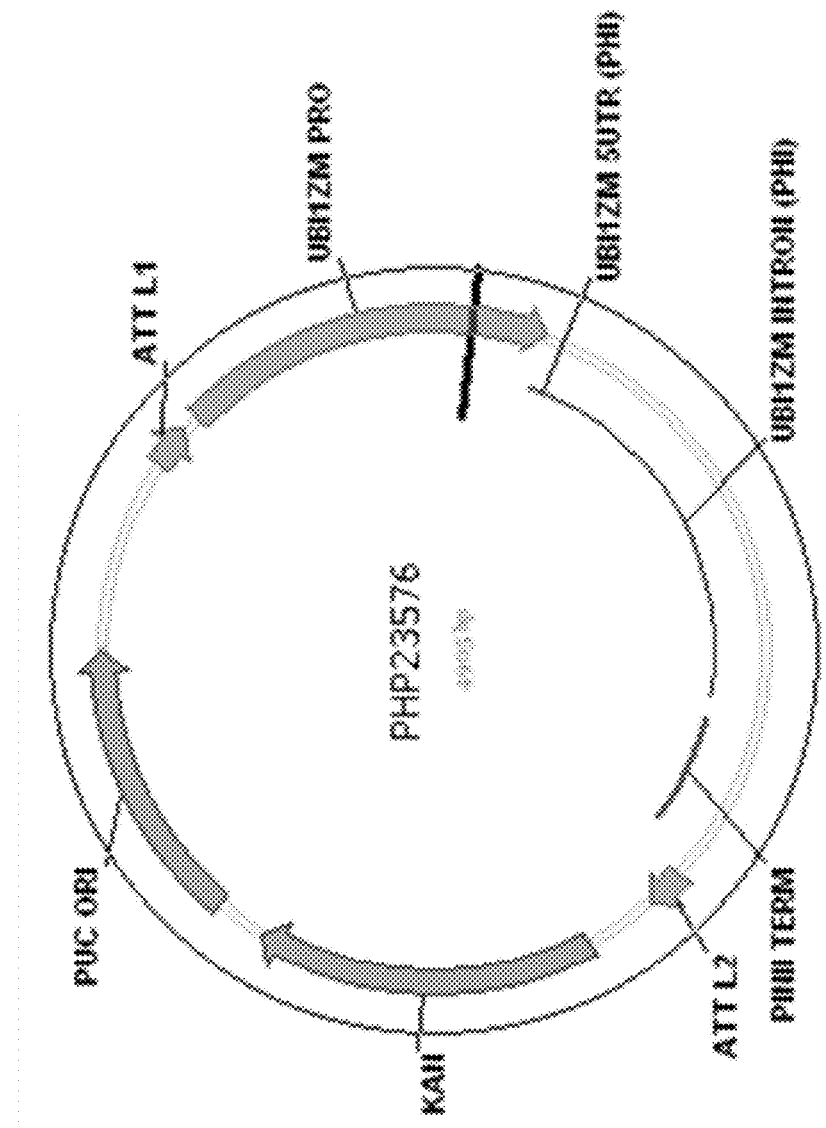
FIG. 5 PHP23576

METHODS AND COMPOSITIONS FOR SILENCING GENE FAMILIES USING ARTIFICIAL MICRORNAS

CROSS REFERENCE TO RELATED APPLICATIONS

This application is a Divisional of U.S. application Ser. No. 13/462,922, filed May 3, 2012, which claims the benefit of U.S. Provisional Application No. 61/484,033, filed May 9, 2011, the entire content of which is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20150520_BB1979USCNT_ST25.txt created on May 20, 2015 and having a size of 64 kilobytes and is filed concurrently with the specification. The sequence listing contained in this ASCII formatted document is part of the specification and is herein incorporated by reference in its entirety.

FIELD OF THE INVENTION

The field of the present invention relates generally to plant molecular biology. More specifically, it relates to constructs and methods to reduce the level of expression of at least two members of a protein and/or gene family in plants.

BACKGROUND OF THE INVENTION

A wide variety of eukaryotic organisms, including plants, animals, and fungi, have evolved several RNA-silencing pathways to protect their cells and genomes against invading nucleic acids, such as viruses or transposons, and to regulate gene expression during development or in response to external stimuli (for review, see Baulcombe (2005) *Trends Biochem Sci* 30: 290-293; Meins et al. (2005) *Annu Rev Cell Dev Biol* 21:297-318). In plants, RNA-silencing pathways have been shown to control a variety of developmental processes including flowering time, leaf morphology, organ polarity, floral morphology, and root development (reviewed by Mallory and Vaucheret (2006) *Nat Genet* 38: S31-36). All RNA-silencing systems involve the processing of double-stranded RNA (dsRNA) into small RNAs of 21 to 25 nucleotides (nt) by an RNaseIII-like enzyme, known as Dicer or Dicer-like in plants (Bernstein et al. (2001) *Nature* 409: 363-366; Xie et al. (2004) *PLoS Biol* 2 E104:0642-0652; Xie et al. (2005) *Proc Natl Acad Sci USA* 102: 12984-12989; Dunoyer et al., (2005) *Nat Genet* 37:1356-1360). These small RNAs are incorporated into silencing effector complexes containing an Argonaute protein (for review, see Meister and Tuschl (2004) *Nature* 431: 343-349).

Artificial microRNAs (amiRNAs) have been described in *Arabidopsis* targeting viral mRNA sequences (Niu et al. (2006) *Nature Biotechnology* 24:1420-1428) or endogenous genes (Schwab et al. (2006) *Plant Cell* 18:1121-1133). The amiRNA construct can be expressed under different promoters in order to change the spatial pattern of silencing (Schwab et al. (2006) *Plant Cell* 18:1121-1133). Artificial miRNAs replace the microRNA and its complementary star sequence in a miRNA precursor backbone and substitute sequences that target an mRNA to be silenced. Silencing by endogenous miRNAs can be found in a variety of spatial, temporal, and developmental expression patterns (Parizotto et al. (2007) *Genes Dev* 18:2237-2242; Alvarez et al. (2006) *Plant Cell* 18:1134-51). Methods and compositions are needed to allow artificial miRNAs to be constructed to both capture and extend the diversity and specificity in the patterns of silencing.

BRIEF SUMMARY OF THE INVENTION

Methods and compositions are provided which allow for a single microRNA (miRNA) to reduce the level of expression of at least two members of the same protein and/or gene family. While a single 21 base pair miRNA can cause cleavage of a variety of species of mRNAs, an entire gene family cannot be silenced unless that gene family shares near identity within a 21 base pair region that is also able to be cleaved by a single miRNA. In certain embodiments, all members of a given protein and/or gene family can be suppressed with a miRNA expression construct disclosed herein even if they do not share near identity within a 21 base pair region that is also able to function as a miRNA. Such methods and compositions employ miRNA expression constructs having a structure such that the most abundant form of miRNA produced from the construct is a 22-nucleotide miRNA. The 22-nucleotide miRNA produced from the miRNA expression construct thereby reduces the level of expression of not only the target sequence for the miRNA, but also reduces the level of expression of at least one additional sequence from the same protein and/or gene family as the target sequence.

BRIEF DESCRIPTION OF THE DRAWINGS

FIG. 1 is a diagram of the PHP46272 plasmid.
FIG. 2 is a diagram of the PHP46271 plasmid.
FIG. 3 is a graph showing that GM-159 FAD2-1B(22) silences both fad2-1 and 2-2 (65% positive). FIG. 3 shows the amount of oleic acid as a percentage of all types of fatty acid. Each data point is representative of a single embryo, and five embryos were assayed from each transgenic event. Wild type embryos typically show between 5-15% oleic acid. An event was considered silenced if three or more somatic embryos showed oleic acid levels greater than 20%.
FIG. 4 is a graph showing that GM-159 FAD2-1B(21) silences only fad2-1 (26% positive). FIG. 4 shows the amount of oleic acid as a percentage of all types of fatty acid. Each data point is representative of a single embryo, and five embryos were assayed from each transgenic event. Wild type embryos typically show between 5-15% oleic acid. An event was considered silenced if three or more somatic embryos showed oleic acid levels greater than 20%.
FIG. 5 is a diagram of the PHP23576 plasmid.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Compositions

Methods and compositions are provided that employ microRNA (miRNA) that, when expressed in a plant or plant cell, is capable of decreasing the expression of multiple proteins/genes in a protein and/or gene family. Such methods and compositions employ miRNA expression constructs. As used herein, a "miRNA expression construct" refers to a DNA construct which comprises a miRNA precursor backbone having a polynucleotide sequence encoding a miRNA and a star sequence. The miRNA expression constructs are designed such that the most abundant miRNA produced from the construct is a 22-nucleotide miRNA.

Canonical miRNAs are 21 nucleotides (21-nt) and arise from symmetric foldback in the stem structure of a hairpin precursor. However, 22-nt miRNAs can be formed by the asymmetric foldback of precursors resulting in a 1 nucleotide bulge in the miRNA strand of the hairpin precursor. A miRNA expression construct, as disclosed herein, is designed to encode a 22-nt miRNA and upon expression in a cell, is capable of reducing the level of mRNA for at least two sequences from the same protein and/or gene family.

"MicroRNA" or "miRNA" refers to oligoribonucleic acid, generally of about 19 to about 24 nucleotides (nt) in length, which regulates expression of a polynucleotide comprising a target sequence. MicroRNAs are non-protein-coding RNAs and have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). MiRNAs are derived, in plants, via dicer-like 1 processing of larger precursor polynucleotides. As discussed in further detail elsewhere herein, a miRNA can be an "artificial miRNA" or "amiRNA" which comprises a miRNA sequence that is synthetically designed to silence a target sequence.

Plant miRNAs regulate endogenous gene expression by recruiting silencing factors to complementary binding sites in target transcripts. MicroRNAs are initially transcribed as long polyadenylated RNAs and are processed to form a shorter sequence that has the capacity to form a stable hairpin and, when further processed by the siRNA machinery, release a miRNA. In plants, both processing steps are carried out by Dicer-like nucleases. miRNAs function by base-pairing to complementary RNA target sequences and trigger RNA cleavage of the target sequence by an RNA-induced silencing complex (RISC).

In a few cases, a small RNA interaction with a target sequence can trigger the production of secondary small interfering RNAs (siRNAs) from the regions surrounding their primary target sites (Sijen et al. (2001) *Cell* 107(4): 465-76). Secondary amplification of the siRNA population and, thus, amplification of the level of gene silencing, occurs via an RNA-dependent RNA polymerase (RDR)-dependent and Dicer-dependent pathway that uses the primary target RNA as a template to generate secondary siRNAs. Newly synthesized double stranded RNA (dsRNA) is subsequently cleaved into siRNAs that are able to guide the degradation of additional secondary target RNAs in a sequence-independent manner. Transitive silencing via this process of generating secondary siRNAs has been observed only in plants and *Caenorhabditis elegans* and only with siRNA and double stranded RNA constructs (Sijen et al., supra; Vaistij et al. (2002) *Plant Cell* 14, 857-867).

A. MicroRNA Expression Constructs Encoding 22-Nucleotide miRNAs

MicroRNA expression constructs encoding a 22-nucleotide (22-nt) miRNA are provided herein. As used herein, a miRNA expression construct comprises a polynucleotide capable of being transcribed into an RNA sequence which is ultimately processed in the cell to form a miRNA. In some embodiments, the miRNA encoded by the miRNA expression construct is an artificial miRNA. Various modifications can be made to the miRNA expression construct to encode a miRNA. Such modifications are discussed in detail elsewhere herein.

In one embodiment, the miRNA expression construct comprises a miRNA precursor backbone having a heterologous miRNA and corresponding star sequence. As used herein, a "miRNA precursor backbone" is a polynucleotide that provides the backbone structure necessary to form a hairpin RNA structure which allows for the processing and ultimate formation of the miRNA. Thus, the miRNA precursor backbones are used as templates for expressing artificial miRNAs and their corresponding star sequence. Within the context of a miRNA expression construct, the miRNA precursor backbone comprises a DNA sequence having the heterologous miRNA and star sequences. When expressed as an RNA, the structure of the miRNA precursor backbone is such as to allow for the formation of a hairpin RNA structure that can be processed into a miRNA. In some embodiments, the miRNA precursor backbone comprises a genomic miRNA precursor sequence, wherein said sequence comprises a native precursor in which a heterologous miRNA and star sequence are inserted.

The miRNA precursor backbones can be from any plant. In some embodiments, the miRNA precursor backbone is from a monocot. In other embodiments, the miRNA precursor backbone is from a dicot. In further embodiments, the backbone is from maize or soybean. MicroRNA precursor backbones have been described previously. For example, US20090155910A1 (WO 2009/079532) discloses the following soybean miRNA precursor backbones: 156c, 159, 166b, 168c, 396b and 398b, and US20090155909A1 (WO 2009/079548) discloses the following maize miRNA precursor backbones: 159c, 164h, 168a, 169r, and 396h. Each of these references is incorporated by reference in their entirety. Non-limiting examples of miRNA precursor backbones disclosed herein include, for example, the miRNA GM-396b precursor backbone (SEQ ID NO: 9) or active variants thereof and the miRNA GM-159 precursor backbone (SEQ ID NO: 16) or active variants thereof. It is recognized that some modifications can be made to the miRNA precursor backbones provided herein, such that the nucleotide sequences maintain at least 60%, 70%, 75%, 80%, 85%, 90%, 95%, 96%, 97%, 98%, 99% or more sequence identity with the nucleotide sequence of the unmodified miRNA precursor backbone. Such variants of a miRNA precursor backbone retain miRNA precursor backbone activity and thereby continue to allow for the processing and ultimate formation of the miRNA.

When designing a miRNA expression construct to target a sequence of interest, the miRNA sequence of the backbone can be replaced with a heterologous miRNA designed to target any sequence of interest. In such instances, the corresponding star sequence in the miRNA expression construct will be altered such that it base pairs with the designed miRNA sequence in the precursor RNA to form an imperfect stem structure. In such instances, both the star sequence and the miRNA sequence are heterologous to the miRNA precursor backbone.

Thus, in one embodiment, the miRNA precursor backbone can be altered to allow for efficient insertion of new miRNA and star sequences within the miRNA precursor backbone. In such instances, the miRNA segment and the star segment of the miRNA precursor backbone are replaced with the heterologous miRNA and the heterologous star sequences using a PCR technique and cloned into an expression plasmid to create the miRNA expression construct. It is recognized that there could be alterations to the position at which the heterologous miRNA and star sequences are inserted into the backbone. Detailed methods for inserting the miRNA and star sequence into the miRNA precursor backbone are described elsewhere herein (see, Examples 4 and 5) and are also described in, for example, US Patent Applications 20090155909A1 and US20090155910A1, herein incorporated by reference in their entirety.

In one embodiment, the miRNA precursor backbone comprises a first polynucleotide segment encoding a miRNA and a second polynucleotide segment encoding a star sequence, wherein the first and second polynucleotide segments are heterologous to the miRNA precursor backbone. As used herein, "heterologous" with respect to a sequence is intended to mean a sequence that originates from a foreign species, or, if from the same species, is substantially modified from its native form in composition and/or genomic locus by deliberate human intervention. For example, with respect to a nucleic acid, it can be a nucleic acid that originates from a foreign species, or is synthetically designed, or, if from the same species, is substantially modified from its native form in composition and/or genomic locus by deliberate human intervention. Thus, in the context of a miRNA expression construct, a heterologous miRNA and star sequence are not native to the miRNA precursor backbone.

The order of the miRNA and the star sequence within the miRNA expression construct can be altered. For example, in specific embodiments, the first polynucleotide segment comprising the miRNA segment of the miRNA expression construct is positioned 5' to the second polynucleotide sequence comprising the star sequence. Alternatively, the second polynucleotide sequence comprising the star sequence can be positioned 5' to the first polynucleotide sequence comprising the miRNA sequence in the miRNA expression construct.

As discussed above, the miRNA expression constructs are designed such that the most abundant form of miRNA produced from the miRNA expression construct is 22-nt in length. Such an expression construct will therefore comprise a first polynucleotide segment comprising the miRNA sequence and a second polynucleotide segment comprising the corresponding star sequence, wherein the star sequence has at least 1-nt less than the polynucleotide encoding the corresponding miRNA. In such instances, having at least 1 less nucleotide in the star sequence will create a mismatch or "bulge" in the miRNA sequence when the star sequence and miRNA sequence hybridize to each other. Such a structure results in a 22-nt miRNA being the most abundant form of miRNA produced. See, Cuperus et al. (2010) *Nature Structural & Mol. Biol.* 17(8):997-1004, herein incorporated by reference in its entirety.

As used herein, by "most abundant form" is meant the 22-nt miRNA represents the largest population of miRNAs produced from the miRNA expression construct. In other words, while the miRNA expression construct may produce miRNAs that are not 22-nt in length (i.e. 19-nt, 20-nt, 21-nt, etc.) the most abundant miRNA produced from the miRNA expression construct is 22-nt in length. Thus, the 22-nt miRNA represents at least 50%, 60%, 70%, 80%, 90%, 95% or 100% or the total miRNA population produced from the miRNA expression construct.

As used herein, a "star sequence" is the sequence within a miRNA precursor backbone that is complementary to the miRNA and forms a duplex with the miRNA to form the stem structure of a hairpin RNA. In some embodiments, the star sequence can comprise less than 100% complementarity to the miRNA sequence. Alternatively, the star sequence can comprise at least 99%, 98%, 97%, 96%, 95%, 90%, 85%, 80% or lower sequence complementarity to the miRNA sequence as long as the star sequence has sufficient complementarity to the miRNA sequence to form a double stranded structure. In still further embodiments, the star sequence comprises a sequence having 1, 2, 3, 4, 5 or more mismatches with the miRNA sequence and still has sufficient complementarity to form a double stranded structure with the miRNA sequence resulting in production of miRNA and suppression of the target sequence.

The most abundant miRNA produced from the miRNA expression construct is 22-nt in length and has sufficient sequence complementarity to a target sequence whose level of RNA is to be reduced. By "sufficient sequence complementarity" to the target sequence is meant that the complementarity is sufficient to allow the 22-nt miRNA to bind to a target sequence and reduce the level of expression of the target sequence. In specific embodiments, a miRNA having sufficient complementarity to the target sequence can share 100% sequence complementarity to the target sequence or it can share less than 100% sequence complementarity (i.e., at least 99%, 98%, 97%, 96%, 95%, 90%, 85%, 80%, 75%, 70% or less sequence complementarity) to the target sequence. In other embodiments, the miRNA can have 1, 2, 3, 4, 5 or up to 6 alterations or mismatches with the target sequence, so long as the 22-nt miRNA has sufficient complementarity to the target sequence to reduce the level of expression of the target sequence. Endogenous miRNAs with multiple mismatches with the target sequence have been reported. For example, see Schawb et al. (2005) *Developmental Cell* 8:517-27 and Cuperus et al. (2010) *Nature Structural and Molecular Biology* 17:997-1003, herein incorporated by reference in their entirety.

When designing a miRNA sequence and star sequence for the miRNA expression constructs disclosed herein, various design choices can be made. See, for example, Schwab R, et al. (2005) *Dev Cell* 8: 517-27. In non-limiting embodiments, the miRNA sequences disclosed herein can have a "U" at the 5'-end, a "C" or "G" at the 19$^{th}$ nucleotide position, and an "A" or "U" at the 10th nucleotide position. In other embodiments, the miRNA design is such that the miRNA have a high free delta-G as calculated using the ZipFold algorithm (Markham, N. R. & Zuker, M. (2005) *Nucleic Acids Res.* 33: W577-W581.) Optionally, a one base pair change can be added within the 5' portion of the miRNA so that the sequence differs from the target sequence by one nucleotide.

A "target sequence" refers to the sequence that the miRNA is designed to reduce and thus the expression of its RNA is to be modulated, e.g., reduced. The region of a target sequence of a gene of interest which is used to design the miRNA may be a portion of an open reading frame, 5' or 3' untranslated region, exon(s), intron(s), flanking region, etc. General categories of genes of interest include, for example, those genes involved in information, such as transcription factors, those involved in communication, such as kinases, and those involved in housekeeping, such as heat shock proteins. More specific categories, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like. The target sequence may be an endogenous sequence, or may be an introduced heterologous sequence.

The 22-nt miRNA produced from the miRNA expression construct is capable of reducing the level of expression of the target sequence and reducing the level of mRNA of the target sequence and at least one additional sequence from the same protein and/or gene family, the members of which would not be reduced by a 21-nt miRNA directed to the same region as the 22-nt miRNA. Methods to assay for reduction in expression of two or more members of a protein and/or gene family include, for example, monitoring for a reduction in mRNA levels from the same protein and/or gene family or monitoring for a change in phenotype. Various ways to assay for a reduction in the expression of two or more members of a protein and/or gene family are discussed elsewhere herein. Thus, as disclosed herein, a single miRNA can silence multiple proteins/genes in a protein and/or gene family or an entire protein and/or gene family.

As used herein, "reducing," "suppression," "silencing," and "inhibition" are used interchangeably to denote the down-regulation of the level of expression of a product of a target sequence relative to its normal expression level in a wild type organism. By "reducing the level of RNA" is intended a reduction in expression by any statistically significant amount including, for example, a reduction of at least 10%, 15%, 20%, 25%, 30%, 35%, 40%, 45%, 50%, 55%, 60%, 65%, 70%, 75%, 80%, 85%, 90%, 95%, or 100% relative to the wild type expression level. The term "expression" as used herein refers to the biosynthesis of a gene product, including the transcription and/or translation of said gene product. Thus, expression of a nucleic acid molecule may refer to transcription of the nucleic acid fragment (e.g., transcription resulting in mRNA or other functional RNA) and/or translation of RNA into a precursor or mature protein (polypeptide).

The miRNAs produced from the miRNA expression constructs disclosed herein can suppress all of the members of a protein and/or gene family or at least 1, 2, 3, 4, 5 or more different sequences within a given protein and/or gene family. As used herein, "gene" refers to a nucleic acid fragment that expresses a specific protein, including regulatory sequences preceding (5' non-coding sequences) and following (3' non-coding sequences) the coding sequence. As used herein, "protein family" and "gene family" are intended to refer to structurally related proteins and nucleic acids, respectively, which are often characterized by conserved structural motifs. Gene family members can be defined according to sequences encoding structurally related polypeptides, or according to nucleic acid sequence identity.

As used herein, sequences from the same protein and/or gene family are structurally related such that the given nucleic acids share at least 60%, 70%, 75%, 80%, 85%, 90%, 91%, 92%, 93%, 94%, 95%, 96%, 97%, 98% or 99% sequence identity with the other sequence from the same gene family, or such that a given polypeptide share at least 60%, 70%, 75%, 80%, 85%, 90%, 91%, 92%, 93%, 94%, 95%, 96%, 97%, 98% or 99% sequence identity with the other sequence from the same protein family, or such that a given polypeptide is encoded by a nucleic acid which share at least 60%, 70%, 75%, 80%, 85%, 90%, 91%, 92%, 93%, 94%, 95%, 96%, 97%, 98% or 99% sequence identity with a polypeptide encoded by a nucleic acid from the same protein family.

In another embodiment, the members of the protein and/or gene family suppressed by the miRNA do not have 21 consecutive nucleotides in common with each other. In such instances, a "traditional" 21-nt miRNA, which is able to silence a sequence having the corresponding 21-nt sequence, would not be able to silence the at least one additional sequence in the protein and/or gene family. As discussed elsewhere herein, the 22-nt miRNAs produced from the instant miRNA expression construct will reduce the level of expression of at least one additional sequence from the same protein and/or gene family as the target sequence.

i. miRNA Expression Constructs Targeting the Galactinol Synthase (GAS) Protein/Gene Family Compositions are provided comprising a miRNA expression construct, wherein the miRNA target sequence is a member of the galactinol synthase (GAS) protein family and wherein the most abundant form of miRNA produced from the miRNA expression construct is a 22-nt miRNA that is capable of reducing the level of mRNA expression of at least one additional member of the GAS protein and/or gene family.

As used herein, "GAS" refers to a gene or encoded protein that influences raffinose family oligosaccharide (RFO) production: the production of galactinol from myo-inositol and UDP-galactose. In soybean, there are at least three classes of GAS genes, corresponding to at least 5 GAS genes. Representative GAS gene sequences include, without limitation, those disclosed in U.S. Application Publication No. 2006/0005280, WO 01/77306, WO 98/50553, and in U.S. Pat. No. 5,648,210, and Sprenger and Keller (2000) *Plant J.* 21:249-258.

Expression of a GAS miRNA expression construct presented herein results in a 22-nt miRNA as the most abundant form of miRNA and silences at least two members of the GAS protein and/or gene family. Methods to determine silencing of GAS genes are known in the art. As discussed elsewhere herein, silencing can be assayed by measuring the level of expression of the target mRNA or protein compared to a control not expressing the miRNA. In addition, GAS gene family silencing can be assayed by measuring the levels of raffinose and stachyose in seeds and somatic embryos and comparing these levels to a control seed or embryo not expressing the 22-nt GAS miRNA. Reducing the level of expression of each GAS family member results in a decrease in accumulation of raffinose and stachyose. Thus, for example, reducing expression of each member of the GAS family can result in a decrease in raffinose family oligosaccharide production to <0.5% of wild type levels. By "decrease" is meant a decrease of at least 1%, 5%, 10%, 20%, 30%, 40%, 50%, 60%, 70%, 80%, 90%, 95%, 99% or more relative to a native control plant, plant part, or cell which did not have the miRNA sequence introduced. For example, Example 7, presented elsewhere herein, provides detailed methods to assay for GAS silencing. Thus, in one embodiment, a miRNA expression construct is provided which, when expressed in a cell, is capable of reducing the level of expression of at least 1, 2, 3, 4, 5 or more members of the GAS protein and/or gene family.

Also provided herein are miRNA precursor backbones which comprise the GAS miRNA and GAS star sequence. A non-limiting miRNA precursor backbone provided herein is, for example, but not limited to, miRNA GM-396b, and has the sequence set forth in SEQ ID NO: 9 or an active variant thereof. The miRNA sequences and star sequences of the backbone can be converted to the artificial GAS miRNA sequences and star sequences using specific PCR primers as described in detail elsewhere herein. Exemplary GAS primers are provided in Table 1 and have the sequences set forth in SEQ ID NOS: 12 and 13.

In a non-limiting embodiment, the GAS miRNA expression construct comprises a miRNA encoded by the sequence set forth in SEQ ID NO:2 or an active variant thereof and a star sequence encoded by the sequence set forth in SEQ ID NO: 6 or an active variant thereof. In another non-limiting embodiment, the GAS miRNA sequence comprises the sequence set forth in SEQ ID NO: 1 or an active variant thereof and the star sequence comprises the sequence set forth in SEQ ID NO: 5 or active variant thereof. An active variant of a given miRNA or star sequence allows for the formation of an active miRNA.

Active variants of the GAS miRNA (i.e. SEQ ID NO: 1), GAS star sequences (i.e. SEQ ID NO: 5), and miRNA precursor backbones are provided herein. The miRNA precursor backbone can be altered, for example, to allow for efficient insertion of new miRNA and star sequences within the miRNA precursor backbone as described elsewhere herein, such that the backbone retains the ability to form a hairpin structure. As discussed elsewhere herein, the miRNA sequence can comprise 1, 2, 3, 4, 5 or up to 6 mismatches with the target sequence and still retain activity and hence, bind to a target sequence and suppress expression of the target sequence. In addition, the star sequence can comprise less than 100% complementarity to the miRNA sequence. The star sequence comprises at least 1 less nucleotide than the miRNA sequence or can comprise a sequence having 1, 2, 3, 4, 5 or more mismatches with the miRNA sequence and still have sufficient complementarity to form a double stranded structure with the miRNA sequence resulting in production of miRNA and suppression of the target sequence.

ii. miRNA Expression Constructs Targeting the Delta 12 Fatty Acid Desaturase-2 (FAD-2) Protein/Gene Family Compositions are provided comprising a miRNA expression construct, wherein the miRNA target sequence is a member of the delta 12 fatty acid desaturase-2 (FAD2) protein and/or gene family, and the most abundant form of miRNA produced from the miRNA expression construct is a 22-nt miRNA that is capable of reducing the level of mRNA expression of at least one additional member of the FAD2 protein and/or gene family.

Delta-12 fatty acid desaturases function in the endoplasmic reticulum to convert oleic acid (18:1) to linoleic acid (18:2). As used herein, "FAD2" refers to a gene or encoded protein capable of catalyzing the insertion of a double bond into a fatty acyl moiety at the twelfth position counted from the carboxyl terminus. There are at least five members of the FAD2 gene family in soybean (Schlueter et al., *Crop Science* 47(S1) (2007)). In soybean the FAD2 genes comprise two subfamilies, FAD2-1 and FAD2-2, each having two gene members (Schlueter et al.). FAD2-1 is primarily expressed in seeds, while FAD2-2 is more generally expressed throughout the plant (Heppard et al. (1996) *Plant Physiology* 110:311-19). Representative FAD2 sequences include, for example, those set forth in U.S. patent application Ser. No. 10/176,149 filed on Jun. 21, 2002, herein incorporated by reference.

Expression of a FAD2 miRNA expression construct presented herein results in a 22-nt miRNA as the most abundant form of miRNA, which reduces the level of expression of at least two or more members of the FAD2 protein and/or gene family. Methods to assay for the silencing of FAD2 genes are known in the art. As discussed elsewhere herein, silencing can be assayed by measuring the level of expression of the target mRNA or protein compared to a control not expressing the miRNA. In addition, FAD2 gene family silencing can be assayed by measuring the levels of oleic acid in seeds and somatic embryos and comparing these levels to a control seed or embryo not expressing the 22-nt FAD2 miRNA. Reducing the level of expression of each member of the FAD2 family results in an increase in accumulation of oleic acid. By "increase" is meant an increase of at least 1%, 5%, 10%, 20%, 30%, 40%, 50%, 60%, 70%, 80%, 90% or more relative to a native control plant, plant part, or cell which did not have the miRNA sequence introduced. For example, Example 8, presented elsewhere herein, provides detailed methods to assay for FAD2 silencing. Thus, in one embodiment, a miRNA construct is provided which when expressed in a cell is capable of reducing the level of expression of at least 1, 2, 3, 4, 5 or more of the FAD2 protein and/or gene family members.

Also provided herein are miRNA precursor backbones which comprise the FAD2 miRNA and FAD2 star sequence. A non-limiting miRNA precursor backbone provided herein is, for example, but not limited to, miRNA GM-159, and has the sequence set forth in SEQ ID NO: 16 or an active variant thereof. The miRNA sequences and star sequences of the backbone can be converted to the artificial FAD2 miRNA sequences and star sequences using specific PCR primers as described in detail elsewhere herein. Exemplary FAD2 primers are provided in Table 1 and have the sequences set forth in SEQ ID NOS: 19 and 20.

In a non-limiting embodiment, the FAD2 miRNA expression construct can comprise a miRNA encoded by the sequence set forth in SEQ ID NO:4 or an active variant thereof and a star sequence encoded by the sequence set forth in SEQ ID NO: 8 or an active variant thereof. In another non-limiting embodiment, the FAD2 miRNA sequence comprises the sequence set forth in SEQ ID NO: 3 or an active variant thereof and the star sequence comprises the sequence set forth in SEQ ID NO: 7 or an active variant thereof.

Active variants of the FAD2 miRNA (i.e. SEQ ID NO: 3), FAD2 star sequences (i.e. SEQ ID NO: 7) and miRNA precursor backbones are provided herein. The miRNA precursor backbone can be altered, for example, to allow for efficient insertion of new miRNA and star sequences within the miRNA precursor backbone as described elsewhere herein, such that the backbone retains the ability to form a hairpin structure. As discussed elsewhere herein, the miRNA sequence can comprise 1, 2, 3, 4, 5 or up to 6 mismatches with the target sequence and still retain activity and hence, bind to a target sequence and suppress expression of the target sequence. In addition, the star sequence can comprise less than 100% complementarity to the miRNA sequence. The star sequence comprises at least 1 less nucleotide than the miRNA sequence or can comprise a sequence having 1, 2, 3, 4, 5 or more mismatches with the miRNA sequence and still have sufficient complementarity to form a double stranded structure with the miRNA sequence resulting in production of miRNA and suppression of the target sequence.

B. Polynucleotides Encoding the miRNA Expression Constructs and Methods of Making Compositions further include isolated or recombinant polynucleotides that encode the miRNA expression constructs, the various components of the miRNA expression constructs, along with the various products of the miRNA expression constructs that are processed into the miRNA. Exemplary components of the miRNA expression constructs include, for example, polynucleotides comprising miRNA precursor backbones, miRNA and star sequences, primers for generating the miRNAs and nucleotide sequences that encode the various RNA sequences. Such polynucleotides are summarized in Table 2. As used herein, "encodes" or "encoding" refers to a DNA sequence which can be processed to generate an RNA and/or polypeptide.

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The compositions provided herein can comprise an isolated or substantially purified polynucleotide. An "isolated" or "purified" polynucleotide is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

Further provided are recombinant polynucleotides comprising the miRNA expression constructs and various components thereof. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. For example, a miRNA expression construct can comprise a miRNA precursor backbone having heterologous polynucleotides comprising the miRNA sequence and the star sequence and, thus the miRNA sequence and star sequence are not native to the miRNA precursor backbone. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

In specific embodiments, one or more of the miRNA expression constructs described herein can be provided in an expression cassette for expression in a plant or other organism or cell type of interest. The cassette can include 5' and 3' regulatory sequences operably linked to a polynucleotide provided herein. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in plants. The regulatory regions (i.e., promoters, transcriptional regulatory regions, and translational termination regions) and/or a recombinant polynucleotide provided herein may be native/analogous to the host cell or to each other. Alternatively, the regulatory regions and/or a recombinant polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide of interest, may be native with the plant host, or may be derived from another source (i.e., foreign or heterologous) to the promoter, the recombinant polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

In preparing the miRNA expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the miRNA expression constructs provided herein. The promoters can be selected based on the desired outcome. It is recognized that different applications can be enhanced by the use of different promoters in the miRNA expression constructs to modulate the timing, location and/or level of expression of the miRNA. Such miRNA expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

In some embodiments, a miRNA expression construct provided herein can be combined with constitutive, tissue-preferred, or other promoters for expression in plants. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a miRNA expression construct within a particular plant tissue. Tissue-preferred promoters are known in the art. See, for example, Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

The expression cassette containing the miRNA expression construct can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D) and sulfonylureas. Additional selectable markers include phenotypic markers such as beta-galactosidase and fluorescent proteins such as green fluorescent protein (GFP) (Su et al. (2004) *Biotechnol. Bioeng.* 85:610-9 and Fetter et al. (2004) *Plant Cell* 16:215-28), cyan fluorescent protein (CYP) (Bolte et al. (2004) *J. Cell Science* 117:943-54 and Kato et al. (2002) *Plant Physiol.* 129:913-42), and yellow fluorescent protein (PhiYFP™ from Evrogen; see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in The Operon, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) Handbook of Experimental Pharmacology, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the compositions presented herein.

C. Plants

Compositions comprising a cell, a transgenic plant cell, a transgenic plant, a transgenic seed, and a transgenic explant comprising a miRNA expression construct are further provided. In one embodiment, a cell, plant, plant cell or plant seed comprise a miRNA expression construct, wherein the most abundant form of miRNA produced from the miRNA expression construct is a 22-nt miRNA that is capable of reducing the level of expression of two or more members of a protein and/or gene family, the members of which would not be reduced by a 21-nt miRNA directed to the same region as the 22-nt miRNA. It is recognized that the miRNA encoded by the miRNA expression construct can target any protein and/or gene family.

In further embodiments, cells, plant cells, plants or seeds comprise a miRNA expression construct comprising a miRNA precursor backbone further comprising a heterologous miRNA sequence and a heterologous star sequence. The miRNA precursor backbone can be from any plant. In some embodiments, the miRNA precursor backbone can be from a monocot (i.e. maize) or a dicot (i.e. soybean). For example, miRNA precursor backbones can comprise, but are not limited to, the miRNA GM-396b precursor backbone (SEQ ID NO: 9) or active variants thereof or the miRNA GM-159 precursor backbone (SEQ ID NO: 16) or active variants thereof.

In other embodiments, cells, plant cells, plants or seeds are provided comprising a miRNA expression construct, wherein the miRNA target sequence is a member of the galactinol synthase (GAS) protein family wherein the most abundant form of miRNA produced from the miRNA expression construct is a 22-nt miRNA that is capable of reducing the level of mRNA expression of at least one additional member of the GAS protein and/or gene family. Reducing the level of expression of GAS family members results in the plant having a decrease in accumulation of raffinose and stachyose as described elsewhere herein.

Further provided are cells, plant cells, plants or seeds comprising a miRNA expression construct, wherein the miRNA target sequence is a member of the delta 12 fatty acid desaturase-2 (FAD2) protein and/or gene family, wherein the most abundant form of miRNA produced from the miRNA expression construct is a 22-nt miRNA that is capable of reducing the level of mRNA expression of at least one additional member of the FAD2 protein and/or gene family. Reducing the level of expression of the FAD2 family members results in the plant having an increase in accumulation of oleic acid as described elsewhere herein.

As used herein, "plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores. The term "plant tissue" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

A transformed plant or transformed plant cell provided herein is one in which genetic alteration, such as transformation, has been affected as to a gene of interest, or is a plant or plant cell which is descended from a plant or cell so altered and which comprises the alteration. A "transgene" is a gene that has been introduced into the genome by a transformation procedure. Accordingly, a "transgenic plant" is a plant that contains a transgene, whether the transgene was introduced into that particular plant by transformation or by breeding; thus, descendants of an originally-transformed plant are encompassed by the definition. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the miRNA, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the miRNA; or (e) the subject plant or plant cell itself, under conditions in which the miRNA expression construct is not expressed.

Plant cells that have been transformed to have a miRNA expression construct provided herein can be grown into whole plants. The regeneration, development, and cultivation of plants from single plant protoplast transformants or from various transformed explants is well known in the art. See, for example, McCormick et al. (1986) *Plant Cell Reports* 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a miRNA expression construct, stably incorporated into their genome.

The miRNA expression constructs provided herein may be used for transformation of any plant species, including, but not limited to, monocots (e.g., maize, sugarcane, wheat, rice, barley, sorghum, or rye) and dicots (e.g., soybean, Brassica, sunflower, cotton, or alfalfa). Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed herein include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants provided herein are crop plants (for example, corn, alfalfa, sunflower, Brassica, soybean, cotton, safflower, peanut, sorghum, wheat, millet, tobacco, etc.). In other embodiments, corn and soybean plants are optimal, and in yet other embodiments soybean plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Depending on the miRNA target sequence, the transgenic plants, plant cells, or seeds expressing a miRNA expression construct provided herein may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified carbohydrate content and/or composition, a modified fatty acid content and/or composition, a modified ability to utilize, partition and/or store nitrogen, and the like.

II. Methods of Introducing

The methods provided herein comprise introducing into a cell, plant cell, plant or seed a miRNA expression construct, wherein the most abundant form of miRNA produced from the miRNA expression construct is a 22-nt miRNA that is capable of reducing the level of expression of the target sequence and of at least one additional member of the same protein and/or gene family, the members of which would not be reduced by a 21-nt miRNA directed to the same region as the 22-nt miRNA. It is recognized that the miRNA encoded by the miRNA expression construct can target any protein and/or gene family.

The miRNA expression constructs that can be introduced into a cell, plant cell, plant or seed comprise a miRNA precursor backbone further comprising a heterologous miRNA sequence and a heterologous star sequence. The miRNA precursor backbone can be from any plant. In some embodiments, the miRNA precursor backbone can be from a monocot (i.e. maize) or a dicot (i.e. soybean). For example, the miRNA precursor backbone can comprise, but is not limited to, the miRNA GM-396b precursor backbone (SEQ ID NO: 9) or active variants thereof or the miRNA GM-159 precursor backbone (SEQ ID NO: 16) or active variants thereof.

In some embodiments, a miRNA expression construct is introduced and comprises a miRNA target sequence that is a member of the galactinol synthase (GAS) protein and/or gene family, wherein the most abundant form of miRNA produced from the miRNA expression construct is a 22-nt miRNA that is capable of reducing the level of mRNA expression of at least one additional member of the GAS protein and/or gene family. In other embodiments, the miRNA expression construct comprises a miRNA target sequence that is a member of the delta 12 fatty acid desaturase-2 (FAD2) protein and/or gene family, wherein the most abundant form of miRNA produced from the miRNA expression construct is a 22-nt miRNA that is capable of reducing the level of mRNA expression of at least one additional member of the FAD2 protein and/or gene family.

The methods provided herein do not depend on a particular method for introducing a sequence into the host cell, only that the polynucleotide gains access to the interior of a least one cell of the host. Methods for introducing polynucleotides into host cells (i.e. plants) are known in the art and include, but are not limited to, stable transformation methods, transient transformation methods, and virus-mediated methods.

The terms "introducing" and "introduced" are intended to mean providing a nucleic acid (e.g., miRNA expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a miRNA expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide is introduced into the host (i.e., a plant) and expressed temporally.

Transformation protocols as well as protocols for introducing polynucleotide sequences into plants may vary depending on the type of plant or plant cell, i.e., monocot or dicot, targeted for transformation. Suitable methods of introducing polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) In *Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413

(rice); Osjoda et al. (1996) *Nature Biotechnology* 14:745-750 (maize via *Agrobacterium tumefaciens*); all of which are herein incorporated by reference.

In specific embodiments, the miRNA expression construct disclosed herein can be provided to a plant using a variety of transient transformation methods. Such transient transformation methods include, but are not limited to, the introduction of the miRNA expression constructs or variants thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, miRNA expression constructs disclosed herein may be introduced into plants by contacting plants with a virus or viral nucleic acids. Generally, such methods involve incorporating a nucleotide construct of the invention within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316, 931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the miRNA expression constructs provided herein can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The miRNA expression construct is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a miRNA expression construct disclosed herein, stably incorporated into their genome is provided.

III. Methods of Use

A method of reducing the level of mRNA of two or more sequences in a cell (e.g. a plant cell) by introducing into the cell a miRNA expression construct is provided. In such methods, the mRNA level of the target sequence and the mRNA level of at least one additional sequence from the same protein and/or gene family as the target sequence are reduced relative to the level of each mRNA in the absence of expression of the miRNA expression construct.

Methods provided herein comprise introducing into a cell (i.e. a plant cell) a miRNA expression construct, wherein the most abundant form of miRNA produced from the miRNA expression construct is a 22-nt miRNA that is capable of reducing the level of expression of two or more members of a protein and/or gene family, the members of which would not be reduced by a 21-nt miRNA directed to the same region as the 22-nt miRNA. Methods further provide a miRNA expression construct comprising a miRNA precursor backbone further comprising a heterologous miRNA sequence and a heterologous star sequence. It is recognized that any miRNA that reduces the level of expression of two or more sequences in the same protein and/or gene family, even if they do not share near identity within a 21 base pair region that is also able to function as a miRNA, could be used in the methods provided herein. Further, any miRNA precursor backbone provided herein (i.e. SEQ ID NOS: 9 or 16 or active variants thereof) can be employed in the provided methods.

In some embodiments, the miRNA target sequence encodes a GAS family member. In such methods, a miRNA expression construct is introduced into a cell, a plant cell, or a plant. The miRNA expression construct comprises a miRNA target sequence that encodes a member of the GAS protein and/or gene family (i.e. SEQ ID NO: 2 or an active variant thereof), wherein the most abundant form of miRNA produced from the miRNA expression construct is a 22-nt miRNA. Thus, the level of expression of the target sequence and at least one additional member of the GAS protein and/or gene family are reduced. In these methods, the resulting phenotype is a decrease in accumulation of raffinose and stachyose as described elsewhere herein.

In other embodiments, the target sequence can be directed to a FAD2 family member. In such methods, a miRNA expression construct is introduced into a cell, a plant cell, or a plant. The miRNA expression construct comprises a miRNA target sequence that encodes a member of the FAD2 protein and/or gene family (i.e. SEQ ID NO: 4 or an active variant thereof), wherein the most abundant form of miRNA produced from the miRNA expression construct is a 22-nt miRNA. Thus, the level of expression of the target sequence and at least one additional member of the FAD2 protein and/or gene family are reduced. In these methods, the resulting phenotype is an increase in accumulation of oleic acid as described elsewhere herein.

In specific embodiments, the miRNA expression constructs disclosed in the methods herein reduce expression of any target sequence or protein and/or gene family of interest in any plant. In specific embodiments, the plant comprises a dicot or a monocot and in further embodiments, the dicot is soybean, *Brassica*, sunflower, cotton or alfalfa and the monocot is maize, sugarcane, wheat, rice, barley, sorghum or rye.

In a particular aspect, a method is provided wherein expression of only one of the two or more sequences of a gene family would be suppressed if a miRNA provided herein was 21 nucleotides in length.

Any appropriate method can be used to assay for a reduced level of expression of two or more sequences from the same protein and/or gene family. For example, evaluation of reduced expression of a target nucleic acid in a plant or plant part, may be accomplished by a variety of means such as Northern analysis of mRNA expression, Western analysis of protein expression, or phenotypic analysis based on the function of the encoded proteins. In some embodiments, levels of other plant by-products such as oil can be analyzed as an indicator of a reduced level of expression of two or more sequences. Expression products of a target nucleic acid can be detected in any of a variety of ways, depending upon the nature of the product (e.g., Western blot and enzyme assay).

IV. Active Variants of the Disclosed Polynucleotides

Active variants of the polynucleotides employed in the compositions and methods are further encompassed. For example, active variants of any of the miRNA expression constructs or one of its components, such as the miRNA precursor backbone, the miRNA, or the star sequence (i.e. SEQ ID NOS: 1-9 and 16) are encompassed herein. "Variants" refer to substantially similar sequences. For polynucleotides, a variant comprises a deletion and/or addition of one or more nucleotides at one or more internal sites within the polynucleotide and/or a substitution of one or more nucleotides at one or more sites in the polynucleotide. Variants of the miRNA expression constructs, miRNA precursor backbones, miRNAs, and/or star sequences disclosed herein may retain activity of the miRNA expression construct, miRNA precursor backbone, miRNA, and/or star sequence as described in detail elsewhere herein. Variant polynucleotides can include synthetically derived polynucleotides, such as those generated, for example, by using site-directed mutagenesis. Generally, variants of a miRNA expression construct, miRNA precursor backbone, miRNA, and/or star sequence (i.e. SEQ ID NOS: 1-9 and 16) disclosed herein will have at least about 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The BLAST programs of Altschul et at (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence provided herein. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

Non-limiting examples of methods and compositions disclosed herein are as follows:

1. An isolated or recombinant polynucleotide capable of being transcribed into an RNA sequence, wherein said polynucleotide comprises a miRNA expression construct, wherein said miRNA expression construct comprises:
   a) a miRNA precursor backbone comprising a first polynucleotide segment encoding a miRNA and a second polynucleotide segment encoding a star sequence;
   b) said first and said second polynucleotide segments are heterologous to the miRNA precursor backbone;
   c) said first polynucleotide segment comprises 22-nucleotides (22-nt) which have sufficient sequence complementary to a target sequence whose level of RNA is to be reduced;
   d) said second polynucleotide segment comprises the complement of the first polynucleotide segment and further comprises at least 1 less nucleotide than said first polynucleotide segment, wherein a 22-nt miRNA is the most abundant form of miRNA produced from said miRNA expression construct; and,
   e) said 22-nt miRNA produced from said miRNA expression construct is capable of reducing the level of mRNA of the target sequence and of at least one additional sequence from the same protein and/or gene family, the members of which would not be reduced by a 21-nt miRNA directed to the same region as the 22-nt miRNA.

2. The isolated or recombinant polynucleotide of embodiment 1, wherein said first polynucleotide segment is 5' to the said second polynucleotide segment.

3. The isolated or recombinant polynucleotide of embodiment 1, wherein said second polynucleotide segment is 5' to the said first polynucleotide segment.

4. The isolated or recombinant polynucleotide of embodiments 1-3, wherein said miRNA precursor backbone is from a plant.

5. The isolated or recombinant polynucleotide of embodiment 4, wherein said plant is a monocot.

6. The isolated or recombinant polynucleotide of embodiment 4, wherein said plant is a dicot.

7. The isolated or recombinant polynucleotide of embodiment 5, wherein said monocot is maize.

8. The isolated or recombinant polynucleotide of embodiment 6, wherein said dicot is soybean.

9. The isolated or recombinant polynucleotide of embodiments 1-4, wherein said miRNA precursor backbone comprises a polynucleotide sequence as set forth in any one of SEQ ID NOS: 9 or 16 or a sequence having at least 90% sequence identity to SEQ ID NOS: 9 or 16, wherein said sequence retains miRNA precursor backbone activity.

10. The isolated or recombinant polynucleotide of any one of embodiments 1-8, wherein said target sequence encodes a member of the galactinol synthase (GAS) protein and/or gene family.

11. The isolated or recombinant polynucleotide of embodiment 10, wherein said first polynucleotide segment comprises the sequence set forth in SEQ ID NO: 2 and the second polynucleotide segment comprises the sequence set forth in SEQ ID NO: 6.

12. The isolated or recombinant polynucleotide of embodiment 10, wherein said miRNA produced from said miRNA expression construct comprises the sequence set forth in SEQ ID NO: 1.

13. The isolated or recombinant polynucleotide of any one of embodiments 1-8, wherein said target sequence encodes a member of the delta 12 fatty acid desaturase 2 protein and/or gene family.

14. The isolated or recombinant polynucleotide of embodiment 13, wherein said first polynucleotide segment comprises the sequence set forth in SEQ ID NO: 4 and the second polynucleotide segment comprises the sequence set forth in SEQ ID NO: 8.

15. The isolated or recombinant polynucleotide of embodiment 13, wherein said miRNA produced from said miRNA expression construct comprises the sequence set forth in SEQ ID NO: 3.

16. A recombinant DNA construct comprising the isolated or recombinant polynucleotide of any one of embodiments 1-15.

17. The recombinant DNA construct of embodiment 16, wherein said recombinant DNA construct comprises a promoter operably linked to the isolated or recombinant polynucleotide.

18. A transformed plant cell comprising the isolated or recombinant polynucleotide of any one of embodiments 1-15.

19. A transformed plant comprising the isolated or recombinant polynucleotide of any one of embodiments 1-15.

20. The transformed plant cell or plant of embodiments 18 or 19, wherein said plant or plant cell or plant is a dicot.

21. The transformed plant cell or plant of embodiment 20, wherein said dicot is soybean, *Brassica*, sunflower, cotton, or alfalfa.

22. The transformed plant cell or plant of embodiment 18 or 19, wherein said plant is a monocot.

23. The transformed plant cell or plant of embodiment 22, wherein said monocot is maize, sugarcane, wheat, rice, barley, sorghum, or rye.

24. A transformed seed of the plant of any one of embodiments 19-23.

25. A method of reducing the level of mRNA of at least two sequences from the same protein and/or gene family in a cell comprising introducing into the cell the recombinant or isolated polynucleotide of any one of embodiments 1-15 or the DNA construct of embodiments 16-17, wherein the expression of said polynucleotide reduces the level of mRNA of each of said at least two sequences relative to the level of mRNA of each of said at least two sequences in the absence of expression of said polynucleotide.

26. The method of embodiment 25, wherein the level of mRNA of only one of said two or more sequences would be reduced if said miRNA was 21 nucleotides in length.

27. The method of embodiments 25 or 26, wherein said cell is a plant cell.

28. The method of any one of embodiments 25-27, wherein said miRNA precursor backbone comprises a polynucleotide sequence as set forth in any one of SEQ ID NO: 9 or 16 or a sequence having at least 90% sequence identity to SEQ ID NOS: 9 or 16, wherein said sequence retains miRNA precursor backbone activity.

29. The method of any one of embodiments 25-26, wherein said target sequence encodes a member of the galactinol synthase (GAS) protein and/or gene family.

30. The method of embodiment 29, wherein said first polynucleotide segment comprises the sequence set forth in SEQ ID NO: 2 and the second polynucleotide segment comprises the sequence set forth in SEQ ID NO: 6.

31. The method of embodiment 30, wherein said miRNA produced from said miRNA expression construct comprises the sequence set forth in SEQ ID NO: 1.

32. The method of any one of embodiments 25-29, wherein said target sequence encodes a member of the delta 12 fatty acid desaturase 2 protein and/or gene family.

33. The method of embodiment 32, wherein said first polynucleotide segment comprises the sequence set forth in SEQ ID NO: 4 and the second polynucleotide segment comprises the sequence set forth in SEQ ID NO: 8.

34. The method of embodiment 33, wherein said miRNA produced from said miRNA expression construct comprises the sequence set forth in SEQ ID NO: 3.

35. The method of any one of embodiments 27-34, wherein said plant is a dicot.

36. The method of embodiment 35, wherein said dicot is soybean, *Brassica*, sunflower, cotton, or alfalfa.

37. The method of any one of embodiments 27-34, wherein said plant is a monocot.

38. The method of embodiment 37, wherein said monocot is maize, sugarcane, wheat, rice, barley, sorghum, or rye.

EXPERIMENTAL

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Design of Artificial MicroRNA Sequences

Artificial microRNAs (amiRNAs) that have the ability to silence multiple genes in a gene family can be designed largely according to rules described in Schwab R, et al. (2005) *Dev Cell* 8: 517-27 except that the amiRNA sequences are 22 nucleotides in length. To summarize, the amiRNA sequences can have a "U" at the 5'-end, a "C" or "G" at the 19$^{th}$ nucleotide position, and an "A" or "U" at the 10th nucleotide position. An additional requirement for artificial microRNA design is that the amiRNA have a high free delta-G as calculated using the ZipFold algorithm (Markham, N. R. & Zuker, M. (2005) *Nucleic Acids Res.* 33: W577-W581.) Optionally, a one base pair change can be added within the 5' portion of the amiRNA so that the sequence differs from the target sequence by one nucleotide.

An amiRNA (SEQ ID NO:1) was designed to silence the GAS genes (the DNA sequence corresponding to this amiRNA is represented by SEQ ID NO:2). Another amiRNA (SEQ ID NO:3) was designed to silence FAD2-1 and FAD2-2 (the DNA sequence corresponding to this amiRNA is represented by SEQ ID NO:4).

Example 2

Design of Artificial Star Sequences

"Star sequences" are those that base pair with the miRNA sequences in the precursor RNA to form imperfect stem structures. Artificial star sequences can be designed by comparing an endogenous precursor structure consisting of a miRNA and an endogenous star sequence with a precursor structure consisting of an amiRNA and an artificial star sequence. The endogenous precursor is folded using mfold (M. Zuker (2003) *Nucleic Acids Res.* 31: 3406-15; and D. H. Mathews, J. et al. (1999) *J. Mol. Biol.* 288: 911-940). Then the miRNA sequence is replaced with the amiRNA sequence, and the endogenous star sequence is replaced with the exact reverse complement of the amiRNA except one base is removed. The removal of this base creates a "bulge" in the miRNA sequence upon folding. The altered sequence is then folded with mfold, and the original and altered structures are compared by eye. If necessary, further alterations to the artificial star sequence can be introduced to maintain the original structure.

An artificial star sequence was designed to silence the GAS genes (SEQ ID NO:5; SEQ ID NO:6 is the DNA sequence corresponding to this artificial star sequence). An artificial star sequence was also designed to silence FAD2-1 and FAD2-2 (SEQ ID NO:7; SEQ ID NO:8 is the DNA sequence corresponding to this artificial star sequence).

Example 3

Conversion of Genomic MicroRNA Precursors to Artificial MicroRNA Precursors

Genomic miRNA precursor genes ("backbones"), such as those described in US20090155909A1 (WO 2009/079548) and in US20090155910A1 (WO 2009/079532), can be converted to amiRNAs using overlapping PCR, and the resulting DNAs can be completely sequenced and then cloned downstream of an appropriate promoter in a vector capable of transformation.

Alternatively, amiRNAs can be synthesized commercially, for example, by Codon Devices (Cambridge, Mass.), DNA 2.0 (Menlo Park, Calif.) or Genescript (Piscataway, N.J.). The synthesized DNA is then cloned downstream of an appropriate promoter in a vector capable of soybean transformation.

Artificial miRNAs can also be constructed using In-Fusion™ technology (Clontech, Mountain View, Calif.) as shown in Examples 4 and 5.

Example 4

Generation of a GAS amiRNA Precursor to Silence Multiple GAS Genes in Soybean The microRNA GM-396b precursor (SEQ ID NO:9) was altered to include Pme I sites immediately flanking the star and microRNA sequences to form the In-Fusion™ ready microRNA GM-396b precursor (SEQ ID NO:10). This sequence was cloned into the Not I site of KS332 (also known as PHP27753) to form the In-Fusion™ ready microRNA GM-396b-KS332 plasmid (SEQ ID NO:11).

The microRNA GM-396b precursor (SEQ ID NO:9) was used as a PCR template with the primers shown in Table 1 (SEQ ID NOs:12 and 13). The primers were designed according to the protocol provided by Clontech and do not leave any footprint of the Pme I sites after the In-Fusion™ recombination reaction. The amplified DNA (SEQ ID NO:14) was recombined into the In-Fusion™ ready microRNA GM-396b-KS332 plasmid (SEQ ID NO:11) digested with Pme I. This was done using protocols provided with the In-Fusion™ kit. The resulting plasmid GM-396b-GAS C(22)/KS322 (also known as PHP46272) is shown in FIG. 1 and is represented by SEQ ID NO:15.

Example 5

Generation of a FAD2 amiRNA Precursor to Silence FAD2-1 and FAD2-2 in Soybean

The microRNA GM-159 precursor (SEQ ID NO:16) was altered to include Pme I sites immediately flanking the star and microRNA sequences to form the In-Fusion™ ready microRNA GM-159 precursor (SEQ ID NO:17). This sequence was cloned into the Not I site of KS332 (also known as PHP27753) to form the In-Fusion™ ready microRNA GM-159-KS332 plasmid (SEQ ID NO:18).

The microRNA GM-159 precursor (SEQ ID NO:16) was used as a PCR template with the primers shown in Table 1 (SEQ ID NOs:19 and 20). The primers were designed according to the protocol provided by Clontech and do not leave any footprint of the Pme I sites after the In-Fusion™ recombination reaction. The amplified DNA (SEQ ID NO:21) was recombined into the In-Fusion™ ready microRNA GM-159-KS332 plasmid (SEQ ID NO:18) digested with Pme I. This was done using protocols provided with the In-Fusion™ kit. The resulting plasmid GM-159-FAD2-1b (22)/KS322 (also known as PHP46271) is shown in FIG. 2 and is represented by SEQ ID NO:22.

TABLE 1

Primers for In-Fusion ™ Inserts

| Primer Name | Sequence | SEQ ID NO: |
|---|---|---|
| GM-159-FAD2-1b (22) priA | aaggggattatgaagcttcccaacccaa ttccctcttgaggatcttactg | 19 |
| GM-159-FAD2-1b (22) priB | aagaagagaagggtgcttcctcaaccct tttccctcagaaggttaatact | 20 |
| GM-396b-GASC (22) priA | tctcaagtcctggtcatgctttcctcat atatatcccaccactcttatgcatcttatatc | 12 |
| GM-396b-GASC (22) priB | cctgaattgccatattctcctcatatat atcccatactctagggcttaaaatcctggag | 13 |

Example 6

Transformation of Soybean

Culture Conditions:

Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 µE/m$^2$/s. Cultures are subcultured every 7 days to 2 weeks by inoculating approximately 35 mg of tissue into 35 mL of fresh liquid SB196 (the preferred subculture interval is every 7 days).

Soybean embryogenic suspension cultures are transformed with soybean expression plasmids by the method of particle gun bombardment (Klein et al., *Nature*, 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment:

Either an intact plasmid or a DNA plasmid fragment containing the delta-5 desaturase genes of interest and the selectable marker gene are used for bombardment. Fragments from soybean expression plasmids comprising the delta-5 desaturase of the present invention are obtained by gel isolation of digested plasmids. The resulting DNA fragments are separated by gel electrophoresis on 1% Sea-Plaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 µL aliquot of sterile distilled water containing 3 mg of gold particles is added to 5 µL of a 1 µg/µL DNA solution (either intact plasmid or DNA fragment prepared as described above), 50 µL 2.5 M $CaCl_2$ and 20 µL of 0.1 M spermidine. The mixture is shaken 3 min on level 3 of a vortex shaker and spun for 10 sec in a bench microfuge. After a wash with 400 µL of 100% ethanol, the pellet is suspended by sonication in 40 µL of 100% ethanol. DNA suspension (5 µL) is dispensed to each flying disk of the Biolistic PDS1000/HE instrument disk. Each 5 µL aliquot contains approximately 0.375 mg gold particles per bombardment (i.e., per disk).

Tissue Preparation and Bombardment with DNA:

Approximately 150-200 mg of 7 day old embryonic suspension cultures is placed in an empty, sterile 60×15 mm petri dish and the dish is covered with plastic mesh. Tissue is bombarded 1 or 2 shots per plate with membrane rupture pressure set at 1100 PSI and the chamber is evacuated to a vacuum of 27-28 inches of mercury. Tissue is placed approximately 3.5 inches from the retaining/stopping screen.

Selection of Transformed Embryos:

Transformed embryos ate selected using hygromycin as the selectable marker. Specifically, following bombardment, the tissue is placed into fresh SB196 media and cultured as described above. Six days post-bombardment, the SB196 is exchanged with fresh SB196 containing 30 mg/L hygromycin. The selection media is refreshed weekly. Four to six weeks post-selection, green, transformed tissue is observed growing from untransformed, necrotic embryogenic clusters. Isolated, green tissue is removed and inoculated into multiwell plates to generate new, clonally propagated, transformed embryogenic suspension cultures.

Embryo Maturation:

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/m$^2$s. After this time embryo clusters are removed to a solid agar media, SB166, for 1-2 weeks. Clusters are then subcultured to medium SB103 for 3 weeks. During this period, individual embryos are removed from the clusters and screened for alterations in their fatty acid compositions as described supra.

Media Recipes:

SB 196—FN Lite Liquid Proliferation Medium (Per Liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |

-continued

| Stock Number | | 1000 mL | 500 mL |
|---|---|---|---|
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g sucrose
2 mL 2,4-D (20 mg/L final concentration)
pH 5.7
8 g TC agar SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g activated charcoal
pH 5.7
2 g gelrite SB 103 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
pH 5.7
2 g gelrite SB 71-4 Solid Medium (Per Liter)

1 bottle Gamborg's B5 salts with sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (Per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

Functional Analysis in Somatic Soybean Embryos

Mature somatic soybean embryos are a good model for zygotic embryos. While in the globular embryo state in liquid culture, somatic soybean embryos contain very low amounts of triacylglycerol (TAG) or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, TAG becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904). The model system is also predictive of the fatty acid composition of seeds from plants derived from transgenic embryos.

Example 7

Assay of GAS Phenotype and Results

Transformations of *Glycine max* cv. Jack were carried out with GM-396b-GAS C(22)/KS322 (FIG. 1; SEQ ID NO:15) and a similar control plasmid designed to produce a 21 nucleotide amiRNA. Both contained artificial microRNA sequences targeted against the galactinol synthase (GAS) genes under the control of a seed specific promoter. Silencing of the GAS genes would be expected to lead to decreased accumulation of raffinose and stachyose in seeds as compared to non-transformed seeds and somatic embryos.

Individual immature soybean embryos were dried-down (by transferring them into an empty small petri dish that was seated on top of a 10 cm petri dish containing some agar gel to allow slow dry down) to mimic the last stages of soybean seed development. Dried-down embryos are capable of producing plants when transferred to soil or soil-less media. Storage products produced by embryos at this stage are similar in composition to storage products produced by zygotic embryos at a similar stage of development, and most importantly, the storage product profile is predictive of plants derived from a somatic embryo line (PCT Publication No. WO 94/11516, which published on May 26, 1994). Raffinose Family Oligosaccharides (raffinose, stachyose) were measured in the transgenic somatic embryos using thin layer chromatography. Somatic embryos were extracted with hexane then dried. The dried material was re-suspended in 80% methanol, incubated at room temperature for 1-2 hours, and centrifuged, and then 2 μl of the supernatant was spotted onto a TLC plate (Kieselgel 60 CF, from EM Scientific, Gibbstown, N.J.; Catalog No. 13749-6). The TLC was run in ethylacetate:isopropanol:20% acetic acid (3:4:4) for 1-1.5 hours. The air dried plates were sprayed with 2% sulfuric acid and heated until the charred sugars were detected.

For each transgenic event produced, four embryos were assayed as described in the above paragraph. The TLC plates were examined visually for the presence or absence of raffinose and stachyose. Events with two or more embryos having no raffinose and no stachyose were considered silenced.

GM-396b-GASC(22) showed a 65% silencing efficiency as compared to GM-396b-GAS C (the same construct except producing only a 21 nucleotide amiRNA), which showed 0% silencing efficiency. These results show that the 22 nucleotide amiRNA precursors are capable of producing amiRNAs that are effective in the silencing of multiple members of the GAS gene family.

Example 8

Assay of Fatty Acid Phenotype and Results

Transformations of Glycine max cv. Jack were carried out with GM-159-FAD2-1b(22)/K5322 (FIG. 2; SEQ ID NO:22) and a similar control plasmid designed to produce a 21 nucleotide amiRNA. Both contained artificial microRNA sequences targeted against fatty acid desaturase 2-1 under the control of a seed specific promoter. Silencing of fatty acid desaturase 2-1 would be expected to lead to somewhat increased levels of oleic acid in somatic embryos and much higher levels of oleic acid in seeds as compared to non-transformed seeds and somatic embryos. Because of the properties of the 22 nucleotide amiRNA it would be expected to silence both FAD2-1 and FAD2-2 which would be expected to lead to increased levels of oleic acid in somatic embryos and in seeds as compared to non-transformed seeds and somatic embryos.

GC analysis of FAME was employed to investigate if amiRNA expression alters the fatty acid profile of soybean somatic embryos. Approximately 5 somatic embryos were analyzed per event and 25-50 events were analyzed per construct. Each somatic embryo was placed in a GC vial. For transesterification, 50 μL of trimethylsulfonium hydroxide (TMSH) was added to the GC vial and then incubated for 30 minutes at room temperature while shaking. Then 0.4 mL of heptane was added to the GC vial and incubated for 30 min at room temperature while shaking Fatty acid methyl esters (54, injected from heptane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

Silencing of fatty acid desaturase leads to an increased level of oleic acid. FIGS. 3 and 4 show the amount of oleic acid as a percentage of all types of fatty acid. Each data point is representative of a single embryo, and five embryos were assayed from each transgenic event. Wild type embryos typically show between 5-15% oleic acid. An event was considered silenced if three or more somatic embryos showed oleic acid levels greater than 20%. Because FAD2-1 and FAD2-2 are expressed in soybean somatic embryos, silencing of FAD2-1 alone would show only slightly elevated levels of oleic acid while silencing of both FAD2-1 and FAD2-2 would show more significant elevated levels of oleic acid. GM-159 FAD2-1B(22) showed a 65% silencing efficiency as compared to GM-159 FAD2-1B (the same construct except producing only a 21 nucleotide amiRNA), which showed only a 26% silencing efficiency (FIGS. 3 and 4). These results show that the 22 nucleotide amiRNA precursors are capable of producing amiRNAs that are effective in gene silencing of more than one FAD2.

Example 9

Generation and Analysis of Seeds with a Silenced Phenotype

Dried down embryos described in Example 6 can be germinated and the plants regenerated. Seeds from transgenic plants can be harvested and assayed for GAS activity, as in Example 7, or for fatty acid content, as in Example 8.

Example 10

22-Nt Artificial MicroRNA (amiRNA) Constructs in Maize 22-nt miRNAs can also be made to silence multiple genes in maize (as described in Example 1), and star sequences can be designed as described in Example 2. In addition, US20090155909A1 (WO 2009/079548) describes maize genomic miRNA precursor sequences that can be converted into effective amiRNAs (Example 3).

The amiRNA cassette can be cloned into an appropriate expression vector, such as PHP23576 (FIG. 5), which contains a ubiquitin promoter-intron and Gateway (Invitrogen) L1 and L2 sites, and the resulting plasmids can be recombined with plasmid PHP20622 (PCT Publication No. WO2006/107,931 published Oct. 12, 2006). The resulting plasmids can then be co-integrated into the LBA4404 Agrobacterium strain LBA4404-containing plasmid PHP10523 and can be used for transformation of maize as described in Example 11.

The resulting transformants can be analyzed phenotypically and compared to non-transformed and control transformed tissue.

Example 11

Transformation of Maize

A. Maize Particle-Mediated DNA Delivery

A DNA construct can be introduced into maize cells capable of growth on suitable maize culture medium. Such competent cells can be from maize suspension culture, callus culture on solid medium, freshly isolated immature embryos or meristem cells. Immature embryos of the Hi-II genotype can be used as the target cells. Ears are harvested at approximately 10 days post-pollination, and 1.2-1.5 mm immature embryos are isolated from the kernels, and placed scutellum-side down on maize culture medium.

The immature embryos are bombarded from 18-72 hours after being harvested from the ear. Between 6 and 18 hours prior to bombardment, the immature embryos are placed on medium with additional osmoticum (MS basal medium, Musashige and Skoog, 1962, Physiol. Plant 15:473-497, with 0.25 M sorbitol). The embryos on the high-osmotic medium are used as the bombardment target, and are left on this medium for an additional 18 hours after bombardment.

For particle bombardment, plasmid DNA (described above) is precipitated onto 1.8 mm tungsten particles using standard CaCl2-spermidine chemistry (see, for example, Klein et al., 1987, Nature 327:70-73). Each plate is bombarded once at 600 PSI, using a DuPont Helium Gun (Lowe et al., 1995, Bio/Technol 13:677-682). For typical media formulations used for maize immature embryo isolation, callus initiation, callus proliferation and regeneration of plants, see Armstrong, C., 1994, In "The Maize Handbook", M. Freeling and V. Walbot, eds. Springer Verlag, NY, pp 663-671.

Within 1-7 days after particle bombardment, the embryos are moved onto N6-based culture medium containing 3 mg/1 of the selective agent bialaphos. Embryos, and later callus, are transferred to fresh selection plates every 2 weeks. The calli developing from the immature embryos are screened for the desired phenotype. After 6-8 weeks, transformed calli are recovered.

B. Transformation of Maize Using *Agrobacterium*

*Agrobacterium*-mediated transformation of maize is performed essentially as described by Zhao et al., in Meth. Mol. Biol. 318:315-323 (2006) (see also Zhao et al., Mol. Breed. 8:323-333 (2001) and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 μE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 μM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L Gelrite®, 100 μM acetosyringone (filter-sterilized), pH 5.8.
3. PHI-C: PHI-B without Gelrite® and acetosyringonee, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 μg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4 D. After two weeks the tissue can be transferred to regeneration medium (Fromm et al., Bio/Technology 8:833 839 (1990)).

TABLE 2

| SEQ ID NO: | RNA/DNA | Description |
| --- | --- | --- |
| 1 | RNA | RNA sequence of the GAS 22 nucleotide amiRNA |
| 2 | DNA | DNA sequence corresponding to the GAS 22 nucleotide amiRNA. |
| 3 | RNA | RNA sequence of the FAD2-1b 22 nucleotide amiRNA. |
| 4 | DNA | DNA sequence corresponding to the FAD2-1b 22 nucleotide amiRNA. |
| 5 | RNA | RNA sequence of the GAS artificial star sequence. |
| 6 | DNA | DNA sequence corresponding to the GAS artificial star sequence. |
| 7 | RNA | RNA sequence of the FAD2-1b artificial star sequence |
| 8 | DNA | DNA sequence corresponding to the FAD2-1b artificial star sequence. |
| 9 | DNA | DNA sequence of the miRNA GM-396b precursor backbone. |
| 10 | DNA | DNA sequence of the In-Fusion™ ready microRNA GM-396b precursor backbone. |
| 11 | DNA | DNA sequence of the In-Fusion™ ready microRNA GM-396b-KS332 plasmid. |

TABLE 2-continued

| SEQ ID NO: | RNA/DNA | Description |
|---|---|---|
| 12 | DNA | Sequence of the GM-396b-GASC(22) priA primer. |
| 13 | DNA | Sequence of the GM-396b-GASC(22) priB primer. |
| 14 | DNA | Sequence of the GM-396b-GAS(22) amplified DNA. |
| 15 | DNA | Sequence of the GM-396b-GAS C(22)/KS322 plasmid (also known as PHP46272; FIG. 1). |
| 16 | DNA | DNA sequence of the miRNA GM-159 precursor backbone. |
| 17 | DNA | DNA sequence of the In-Fusion™ ready microRNA GM-159 precursor backbone. |
| 18 | DNA | DNA sequence of the In-Fusion™ ready microRNA GM-159-KS332 plasmid. |
| 19 | DNA | Sequence of the GM-159-FAD2-1b(22) priA primer. |
| 20 | DNA | Sequence of the GM-159-FAD2-1b(22) priB primer. |
| 21 | DNA | Sequence of the GM-159-FAD2-1B (22) amplified DNA. |
| 22 | DNA | Sequence of the GM-159-FAD2-1b(22)/KS322 plasmid (also known as PHP46271) |

The article "a" and "an" are used herein to refer to one or more than one (i.e., at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of reducing the level of mRNA of at least two sequences from the delta 12 fatty acid desaturase 2 (FAD2) protein and/or gene family in a cell comprising introducing into the cell an isolated or recombinant polynucleotide comprising a miRNA precursor backbone comprising a first polynucleotide segment encoding a miRNA and a second polynucleotide segment encoding a star sequence, wherein:
   a) said first and said second polynucleotide segments are heterologous to the miRNA precursor backbone;
   b) said first polynucleotide segment comprises the sequence set forth in SEQ ID NO:4; and,
   c) said second polynucleotide segment comprises the sequence set forth in SEQ ID NO:8,
   wherein the expression of said polynucleotide reduces the level of mRNA of each of said at least two sequences relative to the level of mRNA of each of said at least two sequences in the absence of expression of said polynucleotide.

2. The method of claim 1, wherein said cell is a plant cell.

3. The method of claim 1, wherein said miRNA precursor backbone comprises a polynucleotide sequence as set forth in any one of SEQ ID NO: 9 or 16 or a sequence having at least 90% sequence identity to SEQ ID NOS: 9 or 16, wherein said sequence retains miRNA precursor backbone activity.

4. The method of claim 1, wherein said miRNA comprises the sequence set forth in SEQ ID NO: 3.

5. The method of claim 2, wherein said plant is a dicot.

6. The method of claim 5, wherein said dicot is soybean, *Brassica*, sunflower, cotton, or alfalfa.

7. The method of claim 2, wherein said plant is a monocot.

8. The method of claim 7, wherein said monocot is maize, sugarcane, wheat, rice, barley, sorghum, or rye.

* * * * *

```
                        SEQUENCE LISTING

<160> NUMBER OF SEQ ID NOS: 22

<210> SEQ ID NO 1
<211> LENGTH: 22
<212> TYPE: RNA
<213> ORGANISM: artificial
<220> FEATURE:
<223> OTHER INFORMATION: GAS amiRNA

<400> SEQUENCE: 1
uccucauaua uaucccacca cu                                              22

<210> SEQ ID NO 2
<211> LENGTH: 22
<212> TYPE: DNA
<213> ORGANISM: artificial
<220> FEATURE:
<223> OTHER INFORMATION: DNA encoding GAS amiRNA

<400> SEQUENCE: 2
tcctcatata tatcccacca ct                                              22

<210> SEQ ID NO 3
<211> LENGTH: 22
<212> TYPE: RNA
<213> ORGANISM: artificial
<220> FEATURE:
<223> OTHER INFORMATION: FAD2 amiRNA

<400> SEQUENCE: 3
ugagggaaaa ggguugagga ag                                              22

<210> SEQ ID NO 4
<211> LENGTH: 22
<212> TYPE: DNA
<213> ORGANISM: artificial
<220> FEATURE:
<223> OTHER INFORMATION: DNA encoding FAD2 amiRNA
```

-continued

<400> SEQUENCE: 4
tgagggaaaa gggttgagga ag                                           22

<210> SEQ ID NO 5
<211> LENGTH: 21
<212> TYPE: RNA
<213> ORGANISM: artificial
<220> FEATURE:
<223> OTHER INFORMATION: GAS artificial star sequence

<400> SEQUENCE: 5
aguaugggau auauaugagg a                                            21

<210> SEQ ID NO 6
<211> LENGTH: 21
<212> TYPE: DNA
<213> ORGANISM: artificial
<220> FEATURE:
<223> OTHER INFORMATION: DNA encoding GAS artificial star sequence

<400> SEQUENCE: 6
agtatgggat atatatgagg a                                            21

<210> SEQ ID NO 7
<211> LENGTH: 21
<212> TYPE: RNA
<213> ORGANISM: artificial
<220> FEATURE:
<223> OTHER INFORMATION: FAD2 artificial star sequence

<400> SEQUENCE: 7
cuucccaacc caauucccuc u                                            21

<210> SEQ ID NO 8
<211> LENGTH: 21
<212> TYPE: DNA
<213> ORGANISM: artificial
<220> FEATURE:
<223> OTHER INFORMATION: DNA encoding FAD2 artificial star sequence

<400> SEQUENCE: 8
cttcccaacc caattccctc t                                            21

<210> SEQ ID NO 9
<211> LENGTH: 590
<212> TYPE: DNA
<213> ORGANISM: Glycine max

<400> SEQUENCE: 9
gcggccgcgc gagaaacttt gtatgggcat ggttatttct cacttctcac cctcctttac     60
tttcttatgc taaatcctcc ttcccctata tctccaccct caacccctttt ttctcattat   120 aacttttggt gcctagatgg tgtgtgtgtg tgcgcgcgag agatctgagc tcaattttcc   180
tctctcaagt cctggtcatg cttttccaca gctttcttga acttcttatg catcttatat   240
ctctccacct ccaggatttt aagccctaga agctcaagaa agctgtggga gaatatggca   300
attcaggctt ttaattgctt tcatttggta ccatcacttg caagatttca gagtacaagg   360
tgaacacaca catcttcctc ttcatcaatt ctctagtttc atccttatct tttcattcac   420
ggtaactctc actaccctct ttcatcttat aagttatacc ggggtgtga tgttgatgag    480 tgtaaattaa atatatgtga tctctttctc tggaaaaatt ttcagtgtga tatacataat   540
aatctcttaa tctagagatt ttatggcttt gttatatata aggcggccgc              590

<210> SEQ ID NO 10
<211> LENGTH: 605
<212> TYPE: DNA
<213> ORGANISM: artificial
<220> FEATURE:
<223> OTHER INFORMATION: In-fusion ready miRNA GM-396b precursor

<400> SEQUENCE: 10

```
gcggccgcgc gagaaacttt gtatgggcat ggttatttct cacttctcac cctcctttac      60
tttcttatgc taaatcctcc ttccactata tctccaccct caaccccttt ttctcattat     120
aacttttggt gcctagatgg tgtgtgtgtg tgcgcgcgag agatctgagc tcaattttcc     180
tctctcaagt cctggtcatg ctgtttaaac cacagctttc ttgaacttct tatgcatctt     240
atatctctcc acctccagga ttttaagccc tagaagctca agaaagctgt gggagtttaa     300
actatggcaa ttcaggcttt taattgcttt catttggtac catcacttgc aagatttcag     360
agtacaaggt gaacacacac atcttcctct tcatcaattc tctagtttca tccttatctt     420
ttcattcacg gtaactctca ctaccctctt tcatcttata agttataccg ggggtgtgat     480
gttgatgagt gtaaattaaa tatatgtgat ctctttctct ggaaaaattt tcagtgtgat     540
atacataata atctcttaat ctagagattt tatggctttg ttatatataa ggaattcgcg     600
gccgc                                                                605
```

<210> SEQ ID NO 11
<211> LENGTH: 10651
<212> TYPE: DNA
<213> ORGANISM: artificial
<220> FEATURE:
<223> OTHER INFORMATION: In-fusion ready miRNA GM-396B-KS332 plasmid
<220> FEATURE:
<221> NAME/KEY: misc_feature
<222> LOCATION: (2349)..(2349)
<223> OTHER INFORMATION: n is a, c, g, or t

<400> SEQUENCE: 11

```
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta accttagcat tgtgaacgag     300
acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actaccattt tatatattat acttatccac     480
ttatttaatg tctttataag gtttgatcca tgatatttct aatattttag ttgatatgta     540
tatgaaaggg tactatttga actctcttac tctgtataaa ggttggatca tccttaaagt     600
gggtctattt aattttattg cttcttacag ataaaaaaaa aattatgagt tggtttgata     660
aaatattgaa ggatttaaaa taataataaa taacatataa tatatgtata taaatttatt     720
ataaatataac atttatctat aaaaaagtaa atattgtcat aaatctatac aatcgtttag     780
ccttgctgga cgaatctcaa ttatttaaac gagagtaaac atatttgact ttttggttat     840
ttaacaaatt attatttaac actatatgaa attttttttt ttatcagcaa agaataaaat     900
taaattaaga aggacaatgg tgtcccaatc cttatacaac caacttccac aagaaagtca     960
agtcagagac aacaaaaaaa caagcaaagg aaattttta atttgagttg tcttgtttgc    1020
```

```
tgcataattt atgcagtaaa acactacaca taacccttttt agcagtagag caatggttga    1080
ccgtgtgctt agcttctttt attttatttt tttatcagca aagaataaat aaaataaaat    1140
gagacacttc agggatgttt caacaagctt ggatcctcga agagaagggt taataacaca    1200
cttttttaac attttttaaca caaattttag ttatttaaaa atttattaaa aaatttaaaa    1260
taagaagagg aactctttaa ataaatctaa cttacaaaat ttatgatttt taataagttt    1320
tcaccaataa aaaatgtcat aaaaatatgt taaaaagtat attatcaata ttctctttat    1380
gataaataaa aagaaaaaaa aaataaaagt taagtgaaaa tgagattgaa gtgactttag    1440
gtgtgtataa atatatcaac cccgccaaca atttatttaa tccaaatata ttgaagtata    1500
ttattccata gcctttatt atttatatat ttattatata aaagctttat ttgttctagg    1560
ttgttcatga atattttttt tggttttatc tccgttgtaa gaaaatcatg tgctttgtgt    1620
cgccactcac tattgcagct ttttcatgca ttggtcagat tgacggttga ttgtattttt    1680
gttttttatg gttttgtgtt atgacttaag tcttcatctc tttatctctt catcaggttt    1740
gatggttacc taatatggtc catgggtaca tgcatggtta aattaggtgg ccaactttgt    1800
tgtgaacgat agaattttt ttatattaag taaactattt ttatattatg aaataataat    1860
aaaaaaaata ttttatcatt attaacaaaa tcatattagt taatttgtta actctataat    1920
aaaagaaata ctgtaacatt cacattacat ggtaacatct ttccaccctt tcatttgttt    1980
tttgtttgat gacttttttt cttgtttaaa tttatttccc ttcttttaaa tttggaatac    2040
attatcatca tatataaact aaaatactaa aaacaggatt acacaaatga taaataataa    2100
cacaaatatt tataaatcta gctgcaatat atttaaacta gctatatcga tattgtaaaa    2160
taaaactagc tgcattgata ctgataaaaa aatatcatgt gctttctgga ctgatgatgc    2220
agtatacttt tgacattgcc tttattttat ttttcagaaa agcttttctta gttctgggtt    2280 cttcattatt tgtttcccat ctccattgtg aattgaatca tttgcttcgt gtcacaaata    2340
caatttagnt aggtacatgc attggtcaga ttcacggttt attatgtcat gacttaagtt    2400
catggtagta cattacctgc cacgcatgca ttatattggt tagatttgat aggcaaattt    2460
ggttgtcaac aatataaata taaataatgt ttttatatta cgaaataaca gtgatcaaaa    2520
caaacagttt tatctttatt aacaagattt tgttttttgtt tgatgacgtt ttttaatgtt    2580 tacgcttttcc cccttctttt gaatttagaa cactttatca tcataaaatc aaatactaaa    2640
aaaattacat atttcataaa taataacaca aatatttta aaaaatctga ataataatg    2700 aacaatatta catattatca cgaaaattca ttaataaaaa tattatataa ataaaatgta    2760
atagtagtta tatgtaggaa aaaagtactg cacgcataat atatacaaaa agattaaaat    2820
gaactattat aaataataac actaaattaa tggtgaatca tatcaaaata atgaaaaagt    2880
aaataaaatt tgtaattaac ttctatatgt attacacaca caataataa ataatagtaa    2940 aaaaaattat gataaatatt taccatctca taagatattt aaaataatga taaaaatata    3000
gattattttt tatgcaacta gctagccaaa aagagaacac gggtatatat aaaaagagta    3060
cctttaaatt ctactgtact tcctttattc ctgacgtttt tatatcaagt ggacatacgt    3120
gaagatttta attatcagtc taaatatttc attagcactt aatactttc tgttttattc    3180 ctatcctata agtagtcccg attctcccaa cattgcttat tcacacaact aactaagaaa    3240
gtcttccata gcccccaag cggcccatgg cctcctccga ggacgtcatc aaggagttca    3300
tgcgcttcaa ggtgcgcatg gagggctccg tgaacggcca cgagttcgag atcgagggcg    3360
agggcgaggg ccgcccctac gagggcaccc agaccgccaa gctgaaggtg accaagggcg    3420
```

```
gcccctgcc cttcgcctgg gacatcctgt cccccagtt ccagtacggc tccaaggtgt    3480
acgtgaagca ccccgccgac atccccgact acaagaagct gtccttcccc gagggcttca    3540
agtgggagcg cgtgatgaac ttcgaggacg gcggcgtggt gaccgtgacc caggactcct    3600
ccctgcagga cggctccttc atctacaagg tgaagttcat cggcgtgaac ttcccctccg    3660
acggccccgt aatgcagaag aagactatgg gctgggaggc ctccaccgag cgcctgtacc    3720
cccgcgacgg cgtgctgaag ggcgagatcc acaaggccct gaagctgaag gacggcggcc    3780
actacctggt ggagttcaag tccatctaca tggccaagaa gcccgtgcag ctgcccggct    3840
actactacgt ggactccaag ctggacatca cctcccacaa cgaggactac accatcgtgg    3900
agcagtacga gcgcgccgag ggccgccacc acctgttcct gtagcggccg ccgcgacac    3960
aagtgtgaga gtactaaata aatgctttgg ttgtacgaaa tcattacact aaataaaata    4020
atcaaagctt atatatgcct tccgctaagg ccgaatgcaa agaaattggt tctttctcgt    4080
tatcttttgc cactttact agtacgtatt aattactact taatcatctt tgtttacggc    4140
tcattatatc cgtcgacggc gcgggccgct ctagaactag tggatccgtc gacggcgcgc    4200
ccgatcatcc ggatatagtt cctcctttca gcaaaaaacc cctcaagacc cgtttagagg    4260
ccccaagggg ttatgctagt tattgctcag cggtggcagc agccaactca gcttcctttc    4320
gggctttgtt agcagccgga tcgatccaag ctgtacctca ctattccttt gccctcggac    4380
gagtgctggg gcgtcggttt ccactatcgg cgagtacttc tacacagcca tcggtccaga    4440
cggccgcgct tctgcgggcg atttgtgtac gcccgacagt cccggctccg atcggacga    4500
ttgcgtcgca tcgaccctgc gcccaagctg catcatcgaa attgccgtca accaagctct    4560
gatagagttg gtcaagacca atgcggagca tatacgcccg agccgcggc gatcctgcaa    4620
gctccggatg cctccgctcg aagtagcgcg tctgctgctc catacaagcc aaccacggcc    4680
tccagaagaa gatgttggcg acctcgtatt gggaatcccc gaacatcgcc tcgctccagt    4740
caatgaccgc tgttatgcgg ccattgtccg tcaggacatt gttggagccg aaatccgcgt    4800
gcacgaggtg ccggacttcg ggcagtcct cggcccaaag catcagctca tcgagagcct    4860
gcgcgacgga cgcactgacg gtgtcgtcca tcacagtttg ccagtgatac acatggggat    4920
cagcaatcgc gcatatgaaa tcacgccatg tagtgtattg accgattcct tgcggtccga    4980
atgggccgaa cccgctcgtc tggctaagat cggccgcagc gatcgcatcc atagcctccg    5040
cgaccggctg cagaacagcg gcagttcgg tttcaggcag gtcttgcaac gtgacaccct    5100
gtgcacggcg ggagatgcaa taggtcaggc tctcgctgaa ttccccaatg tcaagcactt    5160
ccggaatcgg gagcgcggcc gatgcaaagt gccgataaac ataacgatct tgtagaaac    5220
catcggcgca gctatttacc cgcaggacat atccacgccc tcctacatcg aagctgaaag    5280
cacgagattc ttcgccctcc gagagctgca tcaggtcgga gacgctgtcg aacttttcga    5340
tcagaaactt ctcgacagac gtcgcggtga gttcaggctt ttccatgggt atatctcctt    5400
cttaaagtta acaaaatta tttctagagg gaaaccgttg tggtctccct atagtgagtc    5460
gtattaattt cgcgggatcg agatcgatcc aattccaatc ccacaaaaat ctgagcttaa    5520
cagcacagtt gctcctctca gagcagaatc gggtattcaa caccctcata tcaactacta    5580
cgttgtgtat aacggtccac atgccggtat atacgatgac tggggttgta caaaggcggc    5640
aacaaacggc gttcccggag ttgcacacaa gaaatttgcc actattacag aggcaagagc    5700
agcagctgac gcgtacacaa caagtcagca aacagacagg ttgaacttca tccccaaagg    5760
agaagctcaa ctcaagccca agagctttgc taaggcccta acaagcccac caaagcaaaa    5820
```

```
agcccactgg ctcacgctag gaaccaaaag gcccagcagt gatccagccc caaaagagat    5880
ctcctttgcc ccggagatta caatggacga tttcctctat ctttacgatc taggaaggaa    5940
gttcgaaggt gaaggtgacg acactatgtt caccactgat aatgagaagg ttagcctctt    6000
caatttcaga aagaatgctg acccacagat ggttagagag gcctacgcag caggtctcat    6060
caagacgatc tacccgagta caatctccca ggagatcaaa taccttccca agaaggttaa    6120
agatgcagtc aaaagattca ggactaattg catcaagaac acagagaaag acatatttct    6180
caagatcaga agtactattc cagtatggac gattcaaggc ttgcttcata aaccaaggca    6240
agtaatagag attggagtct ctaaaaaggt agttcctact gaatctaagg ccatgcatgg    6300
agtctaagat tcaaatcgag gatctaacag aactcgccgt gaagactggc gaacagttca    6360
tacagagtct tttacgactc aatgacaaga agaaaatctt cgtcaacatg gtggagcacg    6420
acactctggt ctactccaaa aatgtcaaag atacagtctc agaagaccaa agggctattg    6480
agacttttca acaaggata atttcgggaa acctcctcgg attccattgc ccagctatct    6540
gtcacttcat cgaaaggaca gtagaaaagg aaggtggctc ctacaaatgc catcattgcg    6600
ataaaggaaa ggctatcatt caagatgcct ctgccgacag tggtcccaaa gatggacccc    6660
cacccacgag gagcatcgtg gaaaagaag acgttccaac cacgtcttca aagcaagtgg    6720
attgatgtga catctccact gacgtaaggg atgacgcaca atcccactat ccttcgcaag    6780
acccttcctc tatataagga agttcatttc atttggagag acacgctcg agctcatttc    6840 tctattactt cagccataac aaaagaactc ttttctcttc ttattaaacc atgaaaaagc    6900
ctgaactcac cgcgacgtct gtcgagaagt ttctgatcga aaagttcgac agcgtctccg    6960
acctgatgca gctctcggag ggcgaagaat ctcgtgcttt cagcttcgat gtaggagggc    7020
gtggatatgt cctgcgggta aatagctgcg ccgatggttt ctacaaagat cgttatgttt    7080
atcggcactt tgcatcggcc gcgctcccga ttccggaagt gcttgacatt ggggaattca    7140
gcgagagcct gacctattgc atctcccgcc gtgcacaggg tgtcacgttg caagacctgc    7200
ctgaaaccga actgcccgct gttctgcagc cggtcgcgga ggccatggat gcgatcgctg    7260
cggccgatct tagccagacg agcgggttcg gcccattcgg accgcaagga atcggtcaat    7320
acactacatg gcgtgatttc atatgcgcga ttgctgatcc ccatgtgtat cactggcaaa    7380
ctgtgatgga cgacaccgtc agtgcgtccg tcgcgcaggc tctcgatgag ctgatgcttt    7440
gggccgagga ctgccccgaa gtccggcacc tcgtgcacgc ggatttcggc tccaacaatg    7500
tcctgacgga caatggccgc ataacagcgg tcattgactg gagcgaggcg atgttcgggg    7560
attcccaata cgaggtcgcc aacatcttct tctggaggcc gtggttggct tgtatggagc    7620
agcagacgcg ctacttcgag cggaggcatc cggagcttgc aggatcgccg cggctccggg    7680
cgtatatgct ccgcattggt cttgaccaac tctatcagag cttggttgac ggcaatttcg    7740
atgatgcagc ttgggcgcag gtcgatgcg acgcaatcgt ccgatccgga gccgggactg    7800
tcgggcgtac acaaatcgcc cgcagaagcg cggccgtctg gaccgatggc tgtgtagaag    7860
tactcgccga tagtggaaac cgacgcccca gcactcgtcc gagggcaaag gaatagtgag    7920
gtacctaaag aaggagtgcg tcgaagcaga tcgttcaaac atttggcaat aaagtttctt    7980
aagattgaat cctgttgccg gtcttgcgat gattatcata taatttctgt tgaattacgt    8040
taagcatgta ataattaaca tgtaatgcat gacgttattt atgagatggg ttttatgat    8100 tagagtcccg caattataca tttaatacgc gatagaaaac aaaatatagc gcgcaaacta    8160
ggataaatta tcgcgcgcgg tgtcatctat gttactagat cgatgtcgaa tctgatcaac    8220
```

```
ctgcattaat gaatcggcca acgcgcgggg agaggcggtt tgcgtattgg gcgctcttcc   8280
gcttcctcgc tcactgactc gctgcgctcg gtcgttcggc tgcggcgagc ggtatcagct   8340
cactcaaagg cggtaatacg gttatccaca gaatcagggg ataacgcagg aaagaacatg   8400
tgagcaaaag gccagcaaaa ggccaggaac cgtaaaaagg ccgcgttgct ggcgtttttc   8460
cataggctcc gcccccctga cgagcatcac aaaaatcgac gctcaagtca gaggtggcga   8520
aacccgacag gactataaag ataccaggcg tttccccctg gaagctccct cgtgcgctct   8580
cctgttccga ccctgccgct taccggatac ctgtccgcct ttctcccttc gggaagcgtg   8640
gcgctttctc aatgctcacg ctgtaggtat ctcagttcgg tgtaggtcgt tcgctccaag   8700
ctgggctgtg tgcacgaacc ccccgttcag cccgaccgct gcgccttatc cggtaactat   8760
cgtcttgagt ccaacccggt aagacacgac ttatcgccac tggcagcagc cactggtaac   8820
aggattagca gagcgaggta tgtaggcggt gctacagagt tcttgaagtg gtggcctaac   8880
tacggctaca ctagaaggac agtatttggt atctgcgctc tgctgaagcc agttaccttc   8940
ggaaaaagag ttggtagctc ttgatccggc aaacaaacca ccgctggtag cggtggtttt   9000
tttgtttgca agcagcagat tacgcgcaga aaaaaggat ctcaagaaga tcctttgatc    9060
ttttctacgg ggtctgacgc tcagtggaac gaaaactcac gttaagggat tttggtcatg   9120
acattaacct ataaaaatag gcgtatcacg aggccctttc gtctcgcgcg tttcggtgat   9180
gacggtgaaa acctctgaca catgcagctc ccggagacgg tcacagcttg tctgtaagcg   9240
gatgccggga gcagacaagc ccgtcagggc gcgtcagcgg gtgttggcgg gtgtcggggc   9300
tggcttaact atgcggcatc agagcagatt gtactgagag tgcaccatat ggacatattg   9360
tcgttagaac gcggctacaa ttaatacata accttatgta tcatacacat acgatttagg   9420
tgacactata gaacggcgcg ccaagctttt gatccatgcc cttcatttgc cgcttattaa   9480
ttaatttggt aacagtccgt actaatcagt tacttatcct tccccatca taattaatct    9540
tggtagtctc gaatgccaca acactgacta gtctcttgga tcataagaaa aagccaagga   9600
acaaagaag acaaaacaca atgagagtat cctttgcata gcaatgtcta agttcataaa    9660
attcaaacaa aaacgcaatc acacacagtg gacatcactt atccactagc tgatcaggat   9720
cgccgcgtca agaaaaaaaa actggacccc aaaagccatg cacaacaaca cgtactcaca   9780
aaggtgtcaa tcgagcagcc caaaacattc accaactcaa cccatcatga gccctcacat   9840
ttgttgtttc taacccaacc tcaaactcgt attctcttcc gccacctcat ttttgtttat   9900
ttcaacaccc gtcaaactgc atgccacccc gtggccaaat gtccatgcat gttaacaaga   9960
cctatgacta taaatagctg caatctcggc ccaggttttc atcatcaaga accagttcaa  10020
tatcctagta caccgtatta aagaatttaa gatatactgc ggccgcgcga gaaactttgt  10080
atgggcatgg ttatttctca cttctcaccc tcctttactt tcttatgcta atcctccttt  10140
cccctatatc tccaccctca accccttttt ctcattataa cttttggtgc ctagatggtg  10200
tgtgtgtgtg cgcgcgagag atctgagctc aatttcctc tctcaagtcc tggtcatgct    10260
gtttaaacca cagcttcctt gaacttctta tgcatcttat atctctccac ctccaggatt  10320
ttaagcccta gaagctcaag aaagctgtgg gagtttaaac tatggcaatt caggctttta  10380
attgctttca tttggtacca tcacttgcaa gatttcagag tacaaggtga acacacacat  10440
cttcctcttc atcaattctc tagtttcatc cttatctttt cattcacggt aactctcact  10500
accctctttc atcttataag ttataccggg ggtgtgatgt tgatgagtgt aaattaaata  10560
```

```
tatgtgatct ctttctctgg aaaaattttc agtgtgatat acataataat ctcttaatct    10620
agagatttta tggctttgtt atatataagg c                                   10651

<210> SEQ ID NO 12
<211> LENGTH: 55
<212> TYPE: DNA
<213> ORGANISM: artificial
<220> FEATURE:
<223> OTHER INFORMATION: GM-396b-GASC(22) priA

<400> SEQUENCE: 12
tctcaagtcc tggtcatgct ttcctcatat atatcccacc actcttatgc atctt         55

<210> SEQ ID NO 13
<211> LENGTH: 59
<212> TYPE: DNA
<213> ORGANISM: artificial
<220> FEATURE:
<223> OTHER INFORMATION: GM-396b-GASC(22) priB

<400> SEQUENCE: 13
cctgaattgc catattctcc tcatatatat cccatactct agggcttaaa atcctggag     59

<210> SEQ ID NO 14
<211> LENGTH: 126
<212> TYPE: DNA
<213> ORGANISM: artificial
<220> FEATURE:
<223> OTHER INFORMATION: GM-396b-GAS(22) amplified DNA

<400> SEQUENCE: 14
tctcaagtcc tggtcatgct ttcctcatat atatcccacc actcttatgc atcttatatc    60
tctccacctc caggatttta agccctagag tatgggatat atatgaggag aatatggcaa   120
ttcagg                                                              126

<210> SEQ ID NO 15
<211> LENGTH: 10642
<212> TYPE: DNA
<213> ORGANISM: artificial
<220> FEATURE:
<223> OTHER INFORMATION: GM-396b-GASC(22)/KS322 plasmid
<220> FEATURE:
<221> NAME/KEY: misc_feature
<222> LOCATION: (2931)..(2931)
<223> OTHER INFORMATION: n is a, c, g, or t

<400> SEQUENCE: 15
ggccgcgcga gaaactttgt atgggcatgg ttatttctca cttctcaccc tcctttactt    60
tcttatgcta aatcctcctt cccctatatc tccaccctca acccttttt ctcattataa    120 cttttggtgc ctagatggtg tgtgtgtgtg cgcgcgagag atctgagctc aattttcctc   180
tctcaagtcc tggtcatgct ttcctcatat atatcccacc actcttatgc atcttatatc   240
tctccacctc caggatttta agccctagag tatgggatat atatgaggag aatatggcaa   300
ttcaggcttt taattgcttt catttggtac catcacttgc aagatttcag agtacaaggt   360
gaacacacac atcttcctct tcatcaattc tctagtttca tccttatctt ttcattcacg   420
gtaactctca ctaccctctt tcatcttata agttataccg ggggtgtgat gttgatgagt   480
gtaaattaaa tatatgtgat ctctttctct ggaaaaattt tcagtgtgat atacataata   540
atctcttaat ctagagattt tatggctttg ttatatataa gcggccgcaa gtatgaacta   600
aaatgcatgt aggtgtaaga gctcatggag agcatggaat attgtatccg accatgtaac   660
```

```
agtataataa ctgagctcca tctcacttct tctatgaata acaaaggat gttatgatat     720 attaacactc tatctatgca ccttattgtt ctatgataaa tttcctctta ttattataaa    780
tcatctgaat cgtgacggct tatggaatgc ttcaaatagt acaaaaacaa atgtgtacta    840
taagactttc taaacaattc taaccttagc attgtgaacg agacataagt gttaagaaga    900
cataacaatt ataatggaag aagtttgtct ccatttatat attatatatt acccacttat    960
gtattatatt aggatgttaa ggagacataa caattataaa gagagaagtt tgtatccatt    1020
tatatattat atactaccca tttatatatt atacttatcc acttatttaa tgtctttata    1080
aggtttgatc catgatattt ctaatatttt agttgatatg tatatgaaag ggtactattt    1140
gaactctctt actctgtata aaggttggat catccttaaa gtgggtctat ttaattttat    1200
tgcttcttac agataaaaaa aaattatga gttggtttga taaaatattg aaggatttaa    1260
aataataata aataacatat aatatatgta tataaattta ttataatata acatttatct    1320
ataaaaaagt aaatattgtc ataaatctat acaatcgttt agccttgctg gacgaatctc    1380
aattatttaa acgagagtaa acatatttga cttttttggtt atttaacaaa ttattattta   1440
acactatatg aaatttttt tttatcagc aaagaataaa attaaattaa gaaggacaat     1500
ggtgtcccaa tccttataca accaacttcc acaagaaagt caagtcagag acaacaaaaa    1560
aacaagcaaa ggaaattttt taatttgagt tgtcttgttt gctgcataat ttatgcagta    1620
aaacactaca cataacccctt ttagcagtag agcaatggtt gaccgtgtgc ttagcttctt   1680
ttatttattt ttttttatcag caaagaataa ataaaataaa atgagacact tcagggatgt   1740
ttcaacaagc ttggatcctc gaagagaagg gttaataaca cacttttta acattttaa     1800 cacaaattt agttatttaa aaatttatta aaaaatttaa aataagaaga ggaactcttt     1860
aaataaatct aacttacaaa atttatgatt tttaataagt tttcaccaat aaaaaatgtc    1920
ataaaaatat gttaaaaagt atattatcaa tattctcttt atgataaata aaaagaaaaa   1980
aaaaataaaa gttaagtgaa aatgagattg aagtgacttt aggtgtgtat aaatatatca    2040
accccgccaa caatttattt aatccaaata tattgaagta tattattcca tagcctttat    2100
ttatttatat atttattata taaaagcttt atttgttcta ggttgttcat gaaatatttt    2160 tttggttta tctccgttgt aagaaaatca tgtgctttgt gtcgccactc actattgcag     2220 cttttcatg cattggtcag attgacggtt gattgtattt ttgtttttta tggttttgtg     2280
ttatgactta agtcttcatc tctttatctc ttcatcaggt ttgatggtta cctaatatgg    2340
tccatgggta catgcatggt taaattaggt ggccaacttt gttgtgaacg atagaatttt    2400
ttttatatta agtaaactat ttttatatta tgaaataata ataaaaaaa tatttatca     2460 ttattaacaa aatcatatta gttaatttgt taactctata ataaaagaaa tactgtaaca    2520
ttcacattac atggtaacat ctttccaccc tttcatttgt tttttgtttg atgacttttt    2580
ttcttgttta aatttatttc ccttctttta aatttggaat acattatcat catatataaa    2640
ctaaaatact aaaaacagga ttacacaaat gataaataat aacacaaata tttataaatc    2700
tagctgcaat atatttaaac tagctatatc gatattgtaa aataaaacta gctgcattga    2760
tactgataaa aaaatatcat gtgctttctg gactgatgat gcagtatact tttgacattg    2820
cctttatttt attttcaga aaagctttct tagttctggg ttcttcatta tttgtttccc     2880
atctccattg tgaattgaat catttgcttc gtgtcacaaa tacaatttag ntaggtacat    2940
gcattggtca gattcacggt ttattatgtc atgacttaag ttcatggtag tacattacct    3000
gccacgcatg cattatattg gttagatttg ataggcaaat ttggttgtca acaatataaa    3060
```

```
tataaataat gttttatat tacgaaataa cagtgatcaa acaaacagt tttatcttta      3120 ttaacaagat tttgttttg tttgatgacg ttttttaatg tttacgcttt cccccttctt    3180
ttgaatttag aacactttat catcataaaa tcaaatacta aaaaaattac atatttcata   3240
aataataaca caaatatttt taaaaaatct gaaataataa tgaacaatat tacatattat   3300
cacgaaaatt cattaataaa aatattatat aaataaaatg taatagtagt tatatgtagg   3360
aaaaaagtac tgcacgcata atatatacaa aaagattaaa atgaactatt ataaataata   3420
acactaaatt aatggtgaat catatcaaaa taatgaaaaa gtaaataaaa tttgtaatta   3480
acttctatat gtattacaca cacaaataat aaataatagt aaaaaaaatt atgataaata   3540
tttaccatct cataagatat ttaaaataat gataaaaata tagattattt tttatgcaac   3600
tagctagcca aaaagagaac acgggtatat ataaaaagag tacctttaaa ttctactgta   3660
cttcctttat tcctgacgtt tttatatcaa gtggacatac gtgaagattt taattatcag   3720
tctaaatatt tcattagcac ttaatacttt tctgttttat tcctatccta taagtagtcc   3780
cgattctccc aacattgctt attcacacaa ctaactaaga aagtcttcca tagcccccca   3840
agcggcccat ggcctcctcc gaggacgtca tcaaggagtt catgcgcttc aaggtgcgca   3900
tggagggctc cgtgaacggc cacgagttcg agatcgaggg cgagggcgag ggccgcccct   3960
acgagggcac ccagaccgcc aagctgaagg tgaccaaggg cggccccctg cccttcgcct   4020
gggacatcct gtcccccccag ttccagtacg gctccaaggt gtacgtgaag cacccccgccg   4080 acatccccga ctacaagaag ctgtccttcc ccgagggctt caagtgggag cgcgtgatga   4140
acttcgagga cggcggcgtg gtgaccgtga cccaggactc ctccctgcag gacggctcct   4200
tcatctacaa ggtgaagttc atcggcgtga acttcccctc cgacggcccc gtaatgcaga   4260
agaagactat gggctgggag gcctccaccg agcgcctgta ccccgcgac ggcgtgctga   4320 agggcgagat ccacaaggcc ctgaagctga aggacggcgg ccactacctg gtggagttca   4380
agtccatcta catggccaag aagcccgtgc agctgcccgg ctactactac gtggactcca   4440
agctggacat cacctcccac aacgaggact acaccatcgt ggagcagtac gagcgcgccg   4500
agggccgcca ccacctgttc ctgtagcggc cggccgcgac acaagtgtga gagtactaaa   4560
taaatgcttt ggttgtacga aatcattaca ctaaataaaa taatcaaagc ttatatatgc   4620
cttccgctaa ggccgaatgc aaagaaattg gttctttctc gttatctttt gccacttta    4680 ctagtacgta ttaattacta cttaatcatc tttgtttacg gctcattata tccgtcgacg   4740
gcgcgggccg ctctagaact agtggatccg tcgacggcgc gcccgatcat ccggatatag   4800
ttcctccttt cagcaaaaaa cccctcaaga cccgtttaga ggccccaagg ggttatgcta   4860
gttattgctc agcggtggca gcagccaact cagcttcctt tcgggctttg ttagcagccg   4920
gatcgatcca agctgtacct cactattcct ttgccctcgg acgagtgctg ggcgtcggt    4980 ttccactatc ggcgagtact tctacacagc catcggtcca gacggccgcg cttctgcggg   5040
cgatttgtgt acgcccgaca gtcccggctc cggatcggac gattgcgtcg catcgaccct   5100
gcgcccaagc tgcatcatcg aaattgccgt caaccaagct ctgatagagt tggtcaagac   5160
caatgcggag catatacgcc cggagccgcg gcgatcctgc aagctccgga tgcctccgct   5220
cgaagtagcg cgtctgctgc tccatacaag ccaaccacgg cctccagaag aagatgttgg   5280
cgacctcgta ttgggaatcc ccgaacatcg cctcgctcca gtcaatgacc gctgttatgc   5340
ggccattgtc cgtcaggaca ttgttggagc cgaaatccgc gtgcacgagg tgccggactt   5400
cggggcagtc ctcggcccaa agcatcagct catcgagagc ctgcgcgacg gacgcactga   5460
```

```
cggtgtcgtc catcacagtt tgccagtgat acacatgggg atcagcaatc gcgcatatga    5520
aatcacgcca tgtagtgtat tgaccgattc cttgcggtcc gaatgggccg aacccgctcg    5580
tctggctaag atcggccgca gcgatcgcat ccatagcctc cgcgaccggc tgcagaacag    5640
cgggcagttc ggtttcaggc aggtcttgca acgtgacacc ctgtgcacgg cgggagatgc    5700
aataggtcag gctctcgctg aattccccaa tgtcaagcac ttccggaatc gggagcgcgg    5760
ccgatgcaaa gtgccgataa acataacgat ctttgtagaa accatcggcg cagctattta    5820
cccgcaggac atatccacgc cctcctacat cgaagctgaa agcacgagat tcttcgccct    5880
ccgagagctg catcaggtcg agacgctgt cgaacttttc gatcagaaac ttctcgacag    5940
acgtcgcggt gagttcaggc ttttccatgg gtatatctcc ttcttaaagt taaacaaaat    6000
tatttctaga gggaaaccgt tgtggtctcc ctatagtgag tcgtattaat ttcgcgggat    6060
cgagatcgat ccaattccaa tcccacaaaa atctgagctt aacagcacag ttgctcctct    6120
cagagcagaa tcgggtattc aacaccctca tatcaactac tacgttgtgt ataacggtcc    6180
acatgccggt atatacgatg actggggttg tacaaaggcg gcaacaaacg gcgttcccgg    6240
agttgcacac aagaaatttg ccactattac agaggcaaga gcagcagctg acgcgtacac    6300
aacaagtcag caaacagaca ggttgaactt catccccaaa ggagaagctc aactcaagcc    6360
caagagcttt gctaaggccc taacaagccc accaaagcaa aaagcccact ggctcacgct    6420
aggaaccaaa aggcccagca gtgatccagc cccaaaagag atctcctttg ccccggagat    6480
tacaatggac gatttcctct atctttacga tctaggaagg aagttcgaag gtgaaggtga    6540
cgacactatg ttcaccactg ataatgagaa ggttagcctc ttcaatttca gaaagaatgc    6600
tgacccacag atggttagag aggcctacgc agcaggtctc atcaagacga tctacccgag    6660
taacaatctc caggagatca aataccttcc caagaaggtt aaagatgcag tcaaaagatt    6720
caggactaat tgcatcaaga acacagagaa agacatattt ctcaagatca aagtactat    6780 tccagtatgg acgattcaag gcttgcttca taaaccaagg caagtaatag agattggagt    6840
ctctaaaaag gtagttccta ctgaatctaa ggccatgcat ggagtctaag attcaaatcg    6900
aggatctaac agaactcgcc gtgaagactg gcgaacagtt catacagagt cttttacgac    6960
tcaatgacaa gaagaaaatc ttcgtcaaca tggtggagca cgacactctg gtctactcca    7020
aaaatgtcaa agatacagtc tcagaagacc aaagggctat tgagactttt caacaaagga    7080
taatttcggg aaacctcctc ggattccatt gcccagctat ctgtcacttc atcgaaagga    7140
cagtagaaaa ggaaggtggc tcctacaaat gccatcattg cgataaagga aaggctatca    7200
ttcaagatgc ctctgccgac agtggtccca agatggaccc cacccacg aggagcatcg    7260 tggaaaaaga agacgttcca accacgtctt caaagcaagt ggattgatgt gacatctcca    7320
ctgacgtaag ggatgacgca caatcccact atccttcgca agacccttcc tctatataag    7380
gaagttcatt tcatttggag aggacacgct cgagctcatt tctctattac ttcagccata    7440
acaaaagaac tcttttctct tcttattaaa ccatgaaaaa gcctgaactc accgcgacgt    7500
ctgtcgagaa gtttctgatc gaaaagttcg acagcgtctc cgacctgatg cagctctcgg    7560
agggcgaaga atctcgtgct ttcagcttcg atgtaggagg gcgtggatat gtcctgcggg    7620
taaatagctg cgccgatggt ttctacaaag atcgttatgt ttatcggcac tttgcatcgg    7680
ccgcgctccc gattccggaa gtgcttgaca ttggggaatt cagcgagagc ctgacctatt    7740
gcatctcccg ccgtgcacag ggtgtcacgt tgcaagacct gcctgaaacc gaactgcccg    7800
ctgttctgca gccggtcgcg gaggccatgg atgcgatcgc tgcggccgat cttagccaga    7860
```

```
cgagcgggtt cggcccattc ggaccgcaag gaatcggtca atacactaca tggcgtgatt    7920
tcatatgcgc gattgctgat ccccatgtgt atcactggca aactgtgatg gacgacaccg    7980
tcagtgcgtc cgtcgcgcag gctctcgatg agctgatgct ttgggccgag gactgccccg    8040
aagtccggca cctcgtgcac gcggatttcg gctccaacaa tgtcctgacg gacaatggcc    8100
gcataacagc ggtcattgac tggagcgagg cgatgttcgg ggattcccaa tacgaggtcg    8160
ccaacatctt cttctggagg ccgtggttgg cttgtatgga gcagcagacg cgctacttcg    8220
agcggaggca tccggagctt gcaggatcgc cgcggctccg ggcgtatatg ctccgcattg    8280
gtcttgacca actctatcag agcttggttg acggcaattt cgatgatgca gcttgggcgc    8340
agggtcgatg cgacgcaatc gtccgatccg gagccgggac tgtcgggcgt acacaaatcg    8400
cccgcagaag cgcggccgtc tggaccgatg gctgtgtaga agtactcgcc gatagtggaa    8460
accgacgccc cagcactcgt ccgagggcaa aggaatagtg aggtacctaa agaaggagtg    8520
cgtcgaagca gatcgttcaa acatttggca ataaagtttc ttaagattga atcctgttgc    8580
cggtcttgcg atgattatca tataatttct gttgaattac gttaagcatg taataattaa    8640
catgtaatgc atgacgttat ttatgagatg ggttttatg attagagtcc cgcaattata    8700
catttaatac gcgatagaaa acaaaatata gcgcgcaaac taggataaat tatcgcgcgc    8760
ggtgtcatct atgttactag atcgatgtcg aatctgatca acctgcatta atgaatcggc    8820
caacgcgcgg ggagaggcgg tttgcgtatt gggcgctctt ccgcttcctc gctcactgac    8880
tcgctgcgct cggtcgttcg gctgcggcga gcggtatcag ctcactcaaa ggcggtaata    8940
cggttatcca cagaatcagg ggataacgca ggaaagaaca tgtgagcaaa aggccagcaa    9000
aaggccagga accgtaaaaa ggccgcgttg ctggcgtttt tccataggct ccgcccccct    9060
gacgagcatc acaaaaatcg acgctcaagt cagaggtggc gaaacccgac aggactataa    9120
agataccagg cgtttccccc tggaagctcc ctcgtgcgct ctcctgttcc gaccctgccg    9180
cttaccggat acctgtccgc ctttctccct tcgggaagcg tggcgctttc tcaatgctca    9240
cgctgtaggt atctcagttc ggtgtaggtc gttcgctcca agctgggctg tgtgcacgaa    9300
ccccccgttc agcccgaccg ctgcgcctta tccggtaact atcgtcttga gtccaacccg    9360
gtaagacacg acttatcgcc actggcagca gccactggta acaggattag cagagcgagg    9420
tatgtaggcg gtgctacaga gttcttgaag tggtggccta actacggcta cactagaagg    9480
acagtatttg gtatctgcgc tctgctgaag ccagttacct tcggaaaaag agttggtagc    9540
tcttgatccg gcaaacaaac caccgctggt agcggtggtt tttttgtttg caagcagcag    9600
attacgcgca gaaaaaaagg atctcaagaa gatcctttga tcttttctac ggggtctgac    9660
gctcagtgga acgaaaactc acgttaaggg attttggtca tgacattaac ctataaaaat    9720
aggcgtatca cgaggccctt tcgtctcgcg cgtttcggtg atgacggtga aaacctctga    9780
cacatgcagc tcccggagac ggtcacagct tgtctgtaag cggatgccgg gagcagacaa    9840
gcccgtcagg gcgcgtcagc gggtgttggc gggtgtcggg gctggcttaa ctatgcggca    9900
tcagagcaga ttgtactgag agtgcaccat atggacatat tgtcgttaga acgcggctac    9960
aattaataca taaccttatg tatcatacac atacgattta ggtgacacta tagaacggcg    10020
cgccaagctt ttgatccatg cccttcattt gccgcttatt aattaatttg gtaacagtcc    10080
gtactaatca gttacttatc cttccccat cataattaat cttggtagtc tcgaatgcca    10140
caacactgac tagtctcttg gatcataaga aaaagccaag gaacaaaaga agacaaaaca    10200
caatgagagt atcctttgca tagcaatgtc taagttcata aaattcaaac aaaaacgcaa    10260
```

```
tcacacacag tggacatcac ttatccacta gctgatcagg atcgccgcgt caagaaaaaa    10320
aaactggacc ccaaaagcca tgcacaacaa cacgtactca caaaggtgtc aatcgagcag    10380
cccaaaacat tcaccaactc aacccatcat gagccctcac atttgttgtt tctaacccaa    10440
cctcaaactc gtattctctt ccgccacctc attttgttt atttcaacac ccgtcaaact    10500
gcatgccacc ccgtggccaa atgtccatgc atgttaacaa gacctatgac tataaatagc    10560
tgcaatctcg gcccaggttt tcatcatcaa gaaccagttc aatatcctag tacaccgtat    10620
taaagaattt aagatatact gc                                             10642

<210> SEQ ID NO 16
<211> LENGTH: 974
<212> TYPE: DNA
<213> ORGANISM: Glycine max

<400> SEQUENCE: 16
gcggccgctt ctagctagct agggtttggg tagtgagtgt aataaagttg caaagttttt     60
ggttaggtta cgttttgacc ttattattat agttcaaagg gaaacattaa ttaaagggga    120
ttatgaagtg gagctccttg aagtccaatt gaggatctta ctgggtgaat tgagctgctt    180
agctatggat cccacagttc tacccatcaa taagtgcttt tgtggtagtc ttgtggcttc    240
catatctggg gagcttcatt tgcctttata gtattaacct tctttggatt gaagggagct    300
ctacacccct ctcttctttt ctctcataat aatttaaatt tgttatagac tctaaacttt    360
aaatgttttt tttgaagttt ttccgttttt ctcttttgcc atgatcccgt tcttgctgtg    420
gagtaacctt gtccgaggta tgtgcatgat tagatccata cttaatttgt gtgcatcacg    480
aaggtgaggt tgaaatgaac tttgcttttt tgaccttta ggaaagttct tttgttgcag    540
taatcaattt taattagttt taattgacac tattactttt attgtcatct tgttagtttt    600
tattgttgaa ttgagtgcat atttcctagg aaattctctt acctaacatt ttttatacag    660
atctatgctc ttggctcttg cccttactct tggccttgtg ttggttatt gtctacatat    720 ttattgactg gtcgatgaga catgtcacaa ttcttgggct tatttgttgg tctaataaaa    780
ggagtgctta ttgaaagatc aagacggaga ttcggttta taaataaa ctaaagatga    840 catattagtg tgttgatgtc tcttcaggat aatttttgtt tgaaataata tggtaatgtc    900
ttgtctaaat ttgtgtacat aattcttact gatttttgg attgttggat ttttataaac    960
aaatctgcgg ccgc                                                      974

<210> SEQ ID NO 17
<211> LENGTH: 990
<212> TYPE: DNA
<213> ORGANISM: artificial
<220> FEATURE:
<223> OTHER INFORMATION: In-fusion ready miRNA GM-159 precursor

<400> SEQUENCE: 17
gcggccgctt ctagctagct agggtttggg tagtgagtgt aataaagttg caaagttttt     60
ggttaggtta cgttttgacc ttattattat agttcaaagg gaaacattaa ttaaaggga    120 ttatgaagtg tttaaacgga gctccttgaa gtccaattga ggatcttact gggtgaattg    180
agctgcttag ctatggatcc cacagttcta cccatcaata agtgcttttg tggtagtctt    240
gtggcttcca tatctgggga gcttcatttg cctttatagt attaaccttc tttggattga    300
agggagctct agtttaaacc cccttctct tctttttctct cataataatt taaatttgtt    360
atagactcta aactttaaat gttttttttg aagtttttcc gtttttctct tttgccatga    420
```

| | |
|---|---|
| tcccgttctt gctgtggagt aaccttgtcc gaggtatgtg catgattaga tccatactta | 480 |
| atttgtgtgc atcacgaagg tgaggttgaa atgaactttg cttttttgac cttttaggaa | 540 |
| agttcttttg ttgcagtaat caattttaat tagttttaat tgacactatt acttttattg | 600 |
| tcatctttgt tagttttatt gttgaattga gtgcatattt cctaggaaat tctcttacct | 660 |
| aacatttttt atacagatct atgctcttgg ctcttgccct tactcttggc cttgtgttgg | 720 |
| ttatttgtct acatatttat tgactggtcg atgagacatg tcacaattct tgggcttatt | 780 |
| tgttggtcta ataaaaggag tgcttattga agatcaaga cggagattcg gttttatata | 840 |
| aataaactaa agatgacata ttagtgtgtt gatgtctctt caggataatt tttgtttgaa | 900 |
| ataatatggt aatgtcttgt ctaaatttgt gtacataatt cttactgatt ttttggattg | 960 |
| ttggattttt ataaacaaat ctgcggccgc | 990 |

<210> SEQ ID NO 18
<211> LENGTH: 11042
<212> TYPE: DNA
<213> ORGANISM: artificial
<220> FEATURE:
<223> OTHER INFORMATION: In-fusion ready miRNA GM-159-KS332 plasmid
<220> FEATURE:
<221> NAME/KEY: misc_feature
<222> LOCATION: (2349)..(2349)
<223> OTHER INFORMATION: n is a, c, g, or t

<400> SEQUENCE: 18

| | |
|---|---|
| ggccgcaagt atgaactaaa atgcatgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta acaattcta accttagcat tgtgaacgag | 300 |
| acataagtgt taagaagaca taacaattat aatggaagaa gtttgtctcc atttatatat | 360 |
| tatatattac ccacttatgt attatattag gatgttaagg agacataaca attataaaga | 420 |
| gagaagtttg tatccattta tatattatat actacccatt tatatattat acttatccac | 480 |
| ttatttaatg tctttataag gtttgatcca tgatatttct aatattttag ttgatatgta | 540 |
| tatgaaaggg tactatttga actctcttac tctgtataaa ggttggatca tccttaaagt | 600 |
| gggtctattt aattttattg cttcttacag ataaaaaaaa aattatgagt tggtttgata | 660 |
| aaatattgaa ggatttaaaa taataataaa taacatataa tatatgtata taaatttatt | 720 |
| ataatataac atttatctat aaaaaagtaa atattgtcat aaatctatac aatcgtttag | 780 |
| ccttgctgga cgaatctcaa ttatttaaac gagagtaaac atatttgact ttttggttat | 840 |
| ttaacaaatt attatttaac actatatgaa atttttttt ttatcagcaa agaataaaat | 900 |
| taaattaaga aggacaatgg tgtcccaatc cttatacaac caacttccac aagaaagtca | 960 |
| agtcagagac aacaaaaaaa caagcaaagg aaatttttta atttgagttg tcttgtttgc | 1020 |
| tgcataattt atgcagtaaa acactacaca taacccttt agcagtagag caatggttga | 1080 |
| ccgtgtgctt agcttctttt attttatttt tttatcagca aagaataaat aaaataaaat | 1140 |
| gagacacttc agggatgttt caacaagctt ggatcctcga agagaagggt taataacaca | 1200 |
| ctttttttaac atttttaaca caaatttag ttatttaaaa atttattaaa aaattttaaaa | 1260 |
| taagaagagg aactctttaa ataaatctaa cttacaaaat ttatgatttt taataagttt | 1320 |
| tcaccaataa aaaatgtcat aaaaatatgt taaaaagtat attatcaata ttctctttat | 1380 |

```
gataaataaa aagaaaaaaa aaataaaagt taagtgaaaa tgagattgaa gtgactttag    1440
gtgtgtataa atatatcaac cccgccaaca atttatttaa tccaaatata ttgaagtata    1500
ttattccata gcctttattt atttatatat ttattatata aaagctttat tgttctagg     1560 ttgttcatga aatattttt tggttttatc tccgttgtaa gaaaatcatg tgctttgtgt     1620
cgccactcac tattgcagct ttttcatgca ttggtcagat tgacggttga ttgtatttt     1680 gttttttatg gttttgtgtt atgacttaag tcttcatctc tttatctctt catcaggttt    1740
gatggttacc taatatggtc catgggtaca tgcatggtta aattaggtgg ccaactttgt    1800
tgtgaacgat agaattttt ttatattaag taaactattt ttatattatg aaataataat    1860
aaaaaaaata ttttatcatt attaacaaaa tcatattagt taatttgtta actctataat    1920
aaaagaaata ctgtaacatt cacattacat ggtaacatct ttccaccctt tcatttgttt    1980
tttgtttgat gactttttt cttgtttaaa tttatttccc ttcttttaaa tttggaatac    2040
attatcatca tatataaact aaaatactaa aaacaggatt acacaaatga taaataataa    2100
cacaaatatt tataaatcta gctgcaatat atttaaacta gctatatcga tattgtaaaa    2160
taaaactagc tgcattgata ctgataaaaa aatatcatgt gctttctgga ctgatgatgc    2220
agtatacttt tgacattgcc tttattttat ttttcagaaa agcttcctta gttctgggtt    2280
cttcattatt tgtttcccat ctccattgtg aattgaatca tttgcttcgt gtcacaaata    2340
caatttagnt aggtacatgc attggtcaga ttcacggttt attatgtcat gacttaagtt    2400
catggtagta cattacctgc cacgcatgca ttatattggt tagatttgat aggcaaattt    2460
ggttgtcaac aatataaata taataatgt ttttatatta cgaaataaca gtgatcaaaa    2520
caaacagttt tatctttatt aacaagattt tgttttgtt tgatgacgtt ttttaatgtt    2580
tacgctttcc cccttctttt gaatttagaa cactttatca tcataaaatc aaatactaaa    2640
aaaattacat atttcataaa taataacaca atatttta aaaaatctga aataataatg    2700
aacaatatta catattatca cgaaaattca ttaataaaaa tattatataa ataaaatgta    2760
atagtagtta tatgtaggaa aaaagtactg cacgcataat atatacaaaa agattaaaat    2820
gaactattat aaataataac actaaattaa tggtgaatca tatcaaaata atgaaaaagt    2880
aaataaaatt tgtaattaac ttctatatgt attacacaca caaataataa ataatagtaa    2940
aaaaaattat gataaatatt taccatctca taagatattt aaaataatga taaaaatata    3000
gattattttt tatgcaacta gctagccaaa aagagaacac gggtatatat aaaaagagta    3060 ccttttaaatt ctactgtact tccttttattc ctgacgtttt tatatcaagt ggacatacgt    3120 gaagattta attatcagtc taaatatttc attagcactt aatactttc tgttttattc     3180 ctatcctata agtagtcccg attctcccaa cattgcttat tcacacaact aactaagaaa    3240
gtcttccata gcccccaag cggcccatgg cctcctccga ggacgtcatc aaggagttca    3300
tgcgcttcaa ggtgcgcatg gagggctccg tgaacggcca cgagttcgag atcgagggcg    3360
agggcgaggg ccgcccctac gagggcaccc agaccgccaa gctgaaggtg accaagggcg    3420
gccccctgcc cttcgcctgg gacatcctgt ccccccagtt ccagtacggc tccaaggtgt    3480
acgtgaagca ccccgccgac atccccgact acaagaagct gtccttcccc gagggcttca    3540
agtgggagcg cgtgatgaac ttcgaggacg gcggcgtggt gaccgtgacc caggactcct    3600
ccctgcagga cggctccttc atctacaagg tgaagttcat cggcgtgaac ttcccctccg    3660
acggccccgt aatgcagaag aagactatgg gctgggaggc ctccaccgag cgcctgtacc    3720
cccgcgacgg cgtgctgaag ggcgagatcc acaaggccct gaagctgaag gacggcggcc    3780
```

```
actacctggt ggagttcaag tccatctaca tggccaagaa gcccgtgcag ctgcccggct      3840
actactacgt ggactccaag ctggacatca cctcccacaa cgaggactac accatcgtgg      3900
agcagtacga gcgcgccgag ggccgccacc acctgttcct gtagcggccg gccgcgacac      3960
aagtgtgaga gtactaaata aatgctttgg ttgtacgaaa tcattacact aaataaaata      4020
atcaaagctt atatatgcct tccgctaagg ccgaatgcaa agaaattggt tctttctcgt      4080
tatcttttgc cacttttact agtacgtatt aattactact taatcatctt tgtttacggc      4140
tcattatatc cgtcgacggc gcgggccgct ctagaactag tggatccgtc gacggcgcgc      4200
ccgatcatcc ggatatagtt cctcctttca gcaaaaaacc cctcaagacc cgtttagagg      4260
ccccaagggg ttatgctagt tattgctcag cggtggcagc agccaactca gcttccttc     4320 gggctttgtt agcagccgga tcgatccaag ctgtacctca ctattccttt gccctcggac      4380
gagtgctggg gcgtcggttt ccactatcgg cgagtacttc tacacagcca tcggtccaga      4440
cggccgcgct tctgcgggcg atttgtgtac gcccgacagt cccggctccg gatcggacga      4500
ttgcgtcgca tcgaccctgc gcccaagctg catcatcgaa attgccgtca accaagctct      4560
gatagagttg gtcaagacca atgcggagca tatacgcccg gagccgcggc gatcctgcaa      4620
gctccggatg cctccgctcg aagtagcgcg tctgctgctc catacaagcc aaccacggcc      4680
tccagaagaa gatgttggcg acctcgtatt gggaatcccc gaacatcgcc tcgctccagt      4740
caatgaccgc tgttatgcgg ccattgtccg tcaggacatt gttggagccg aaatccgcgt      4800
gcacgaggtg ccggacttcg gggcagtcct cggcccaaag catcagctca tcgagagcct      4860
gcgcgacgga cgcactgacg gtgtcgtcca tcacagtttg ccagtgatac acatggggat      4920
cagcaatcgc gcatatgaaa tcacgccatg tagtgtattg accgattcct tgcggtccga      4980
atgggccgaa cccgctcgtc tggctaagat cggccgcagc gatcgcatcc atagcctccg      5040
cgaccggctg cagaacagcg ggcagttcgg tttcaggcag gtcttgcaac gtgacaccct      5100
gtgcacggcg ggagatgcaa taggtcaggc tctcgctgaa ttccccaatg tcaagcactt      5160
ccggaatcgg gagcgcggcc gatgcaaagt gccgataaac ataacgatct ttgtagaaac      5220
catcggcgca gctatttacc cgcaggacat atccacgccc tcctacatcg aagctgaaag      5280
cacgagattc ttcgccctcc gagagctgca tcaggtcgga gacgctgtcg aacttttcga      5340
tcagaaactt ctcgacagac gtcgcggtga gttcaggctt ttccatgggt atatctcctt      5400
cttaaagtta aacaaaatta tttctagagg gaaaccgttg tggtctccct atagtgagtc      5460
gtattaattt cgcgggatcg agatcgatcc aattccaatc ccacaaaaat ctgagcttaa      5520
cagcacagtt gctcctctca gagcagaatc gggtattcaa caccctcata tcaactacta      5580
cgttgtgtat aacggtccac atgccggtat atacgatgac tggggttgta caaaggcggc      5640
aacaaacggc gttcccggag ttgcacacaa gaaatttgcc actattacag aggcaagagc      5700
agcagctgac gcgtacacaa caagtcagca aacagacagg ttgaacttca tccccaaagg      5760
agaagctcaa ctcaagccca agagctttgc taaggcccta acaagcccac caaagcaaaa      5820
agcccactgg ctcacgctag gaaccaaaag gcccagcagt gatccagccc caaaagagat      5880
ctcctttgcc ccgagattaa caatggacga tttcctctat ctttacgatc taggaaggaa      5940
gttcgaaggt gaaggtgacg acactatgtt caccactgat aatgagaagg ttagcctctt      6000
caatttcaga aagaatgctg acccacagat ggttagagag gcctacgcag caggtctcat      6060
caagacgatc tacccgagta caatctccag ggagatcaaa taccttccca agaaggttaa      6120
agatgcagtc aaaagattca ggactaattg catcaagaac acagagaaag acatatttct      6180
```

```
caagatcaga agtactattc cagtatggac gattcaaggc ttgcttcata aaccaaggca    6240
agtaatagag attggagtct ctaaaaaggt agttcctact gaatctaagg ccatgcatgg    6300
agtctaagat tcaaatcgag gatctaacag aactcgccgt gaagactggc gaacagttca    6360
tacagagtct tttacgactc aatgacaaga agaaaatctt cgtcaacatg gtggagcacg    6420
acactctggt ctactccaaa aatgtcaaag atacagtctc agaagaccaa agggctattg    6480
agacttttca acaaaggata atttcgggaa acctcctcgg attccattgc ccagctatct    6540
gtcacttcat cgaaaggaca gtagaaaagg aaggtggctc ctacaaatgc catcattgcg    6600
ataaaggaaa ggctatcatt caagatgcct ctgccgacag tggtcccaaa gatggacccc    6660
cacccacgag gagcatcgtg gaaaagaag acgttccaac cacgtcttca aagcaagtgg     6720
attgatgtga catctccact gacgtaaggg atgacgcaca atcccactat ccttcgcaag    6780
acccttcctc tatataagga agttcatttc atttggagag gacacgctcg agctcatttc    6840
tctattactt cagccataac aaaagaactc ttttctcttc ttattaaacc atgaaaagc     6900 ctgaactcac cgcgacgtct gtcgagaagt ttctgatcga aaagttcgac agcgtctccg    6960
acctgatgca gctctcggag ggcgaagaat ctcgtgcttt cagcttcgat gtaggagggc    7020
gtggatatgt cctgcgggta aatagctgcg ccgatggttt ctacaaagat cgttatgttt    7080
atcggcactt tgcatcggcc gcgctcccga ttccggaagt gcttgacatt ggggaattca    7140
gcgagagcct gacctattgc atctcccgcc gtgcacaggg tgtcacgttg caagacctgc    7200
ctgaaaccga actgcccgct gttctgcagc cggtcgcgga ggccatggat gcgatcgctg    7260
cggccgatct tagccagacg agcgggttcg gcccattcgg accgcaagga atcggtcaat    7320
acactacatg gcgtgatttc atatgcgcga ttgctgatcc ccatgtgtat cactggcaaa    7380
ctgtgatgga cgacaccgtc agtgcgtccg tcgcgcaggc tctcgatgag ctgatgcttt    7440
gggccgagga ctgccccgaa gtccggcacc tcgtgcacgc ggatttcggc tccaacaatg    7500
tcctgacgga caatggccgc ataacagcgg tcattgactg gagcgaggcg atgttcgggg    7560
attcccaata cgaggtcgcc aacatcttct tctggaggcc gtggttggct tgtatggagc    7620
agcagacgcg ctacttcgag cggaggcatc cggagcttgc aggatcgccg cggctccggg    7680
cgtatatgct ccgcattggt cttgaccaac tctatcagag cttggttgac ggcaatttcg    7740
atgatgcagc ttgggcgcag ggtcgatgcg acgcaatcgt ccgatccgga gccgggactg    7800
tcgggcgtac acaaatcgcc cgcagaagcg cggccgtctg gaccgatggc tgtgtagaag    7860
tactcgccga tagtggaaac cgacgcccca gcactcgtcc gagggcaaag gaatagtgag    7920
gtacctaaag aaggagtgcg tcgaagcaga tcgttcaaac atttggcaat aaagtttctt    7980
aagattgaat cctgttgccg gtcttgcgat gattatcata taatttctgt tgaattacgt    8040
taagcatgta ataattaaca tgtaatgcat gacgttattt atgagatggg tttttatgat    8100
tagagtcccg caattataca tttaatacgc gatagaaaac aaaatatagc gcgcaaacta    8160
ggataaatta tcgcgcgcgg tgtcatctat gttactagat cgatgtcgaa tctgatcaac    8220
ctgcattaat gaatcggcca acgcgcgggg agaggcggtt tgcgtattgg gcgctcttcc    8280
gcttcctcgc tcactgactc gctgcgctcg gtcgttcggc tgcggcgagc ggtatcagct    8340
cactcaaagg cggtaatacg gttatccaca gaatcagggg ataacgcagg aaagaacatg    8400
tgagcaaaag gccagcaaaa ggccaggaac cgtaaaaagg ccgcgttgct ggcgtttttc    8460
cataggctcc gcccccctga cgagcatcac aaaaatcgac gctcaagtca gaggtggcga    8520
aacccgacag gactataaag ataccaggcg tttccccctg gaagctccct cgtgcgctct    8580
```

```
cctgttccga ccctgccgct taccggatac ctgtccgcct ttctcccttc gggaagcgtg    8640
gcgctttctc aatgctcacg ctgtaggtat ctcagttcgg tgtaggtcgt tcgctccaag    8700
ctgggctgtg tgcacgaacc ccccgttcag cccgaccgct gcgccttatc cggtaactat    8760
cgtcttgagt ccaacccggt aagacacgac ttatcgccac tggcagcagc cactggtaac    8820
aggattagca gagcgaggta tgtaggcggt gctacagagt tcttgaagtg gtggcctaac    8880
tacggctaca ctagaaggac agtatttggt atctgcgctc tgctgaagcc agttaccttc    8940 ggaaaagag  ttggtagctc ttgatccggc aaacaaacca ccgctggtag cggtggtttt    9000
tttgtttgca agcagcagat tacgcgcaga aaaaaggat  ctcaagaaga tcctttgatc    9060
ttttctacgg ggtctgacgc tcagtggaac gaaaactcac gttaagggat tttggtcatg    9120
acattaacct ataaaaatag gcgtatcacg aggccctttc gtctcgcgcg tttcggtgat    9180
gacggtgaaa acctctgaca catgcagctc ccggagacgg tcacagcttg tctgtaagcg    9240
gatgccggga gcagacaagc ccgtcagggc gcgtcagcgg gtgttggcgg gtgtcggggc    9300
tggcttaact atgcggcatc agagcagatt gtactgagag tgcaccatat ggacatattg    9360
tcgttagaac gcggctacaa ttaatacata accttatgta tcatacacat acgatttagg    9420
tgacactata gaacggcgcg ccaagctttt gatccatgcc cttcatttgc cgcttattaa    9480
ttaatttggt aacagtccgt actaatcagt tacttatcct tcccccatca taattaatct    9540
tggtagtctc gaatgccaca acactgacta gtctcttgga tcataagaaa aagccaagga    9600 acaaagaag  acaaaacaca atgagagtat cctttgcata gcaatgtcta agttcataaa    9660
attcaaacaa aaacgcaatc acacacagtg gacatcactt atccactagc tgatcaggat    9720
cgccgcgtca agaaaaaaaa actggacccc aaaagccatg cacaacaaca cgtactcaca    9780
aaggtgtcaa tcgagcagcc caaaacattc accaactcaa cccatcatga gccctcacat    9840
ttgttgtttc taacccaacc tcaaactcgt attctcttcc gccacctcat ttttgtttat    9900
ttcaacaccc gtcaaactgc atgccacccc gtggccaaat gtccatgcat gttaacaaga    9960
cctatgacta taaatagctg caatctcggc ccaggttttc atcatcaaga accagttcaa   10020
tatcctagta caccgtatta aagaatttaa gatatactgc ggccgcttct agctagctag   10080
ggtttgggta gtgagtgtaa taaagttgca agttttttgg ttaggttacg ttttgacctt   10140
attattatag ttcaaaggga aacattaatt aaagggggatt atgaagtgtt taaacgagc   10200 tccttgaagt ccaattgagg atcttactgg gtgaattgag ctgcttagct atggatccca   10260
cagttctacc catcaataag tgcttttgtg gtagtcttgt ggcttccata tctggggagc   10320
ttcatttgcc tttatagtat taaccttctt tggattgaag ggagctctag tttaaaccac   10380
ccttctcttc ttttctctca taataattta aatttgttat agactctaaa ctttaaatgt   10440 ttttttttgaa gttttttccgt ttttctcttt tgccatgatc ccgttcttgc tgtggagtaa   10500
ccttgtccga ggtatgtgca tgattagatc catacttaat ttgtgtgcat cacgaaggtg   10560
aggttgaaat gaactttgct ttttttgacct tttaggaaag ttctttttgtt gcagtaatca   10620 attttaatta gttttaattg acactattac ttttattgtc atctttgtta gttttattgt   10680
tgaattgagt gcatatttcc taggaaattc tcttacctaa catttttttat acagatctat   10740 gctcttggct cttgccctta ctcttggcct tgtgttggtt atttgtctac atatttattg   10800
actggtcgat gagacatgtc acaattcttg ggcttatttg ttggtctaat aaaaggagtg   10860
cttattgaaa gatcaagacg gagattcggt tttatataaa taaactaaag atgacatatt   10920
agtgtgttga tgtctcttca ggataatttt tgtttgaaat aatatggtaa tgtcttgtct   10980
```

```
aaatttgtgt acataattct tactgatttt ttggattgtt ggattttat aaacaaatct    11040 gc                                                                  11042

<210> SEQ ID NO 19
<211> LENGTH: 50
<212> TYPE: DNA
<213> ORGANISM: artificial
<220> FEATURE:
<223> OTHER INFORMATION: GM-159-FAD2-1b(22)priA

<400> SEQUENCE: 19
aaggggatta tgaagcttcc caacccaatt ccctcttgag gatcttactg                50

<210> SEQ ID NO 20
<211> LENGTH: 50
<212> TYPE: DNA
<213> ORGANISM: artificial
<220> FEATURE:
<223> OTHER INFORMATION: GM-159-FAD2-1b(22)priB

<400> SEQUENCE: 20
aagaagagaa gggtgcttcc tcaacccttt tccctcagaa ggttaatact                50

<210> SEQ ID NO 21
<211> LENGTH: 206
<212> TYPE: DNA
<213> ORGANISM: artificial
<220> FEATURE:
<223> OTHER INFORMATION: GM-159-FAD2-1B(22) amplified DNA

<400> SEQUENCE: 21
aaggggatta tgaagcttcc caacccaatt ccctcttgag gatcttactg ggtgaattga     60
gctgcttagc tatggatccc acagttctac ccatcaataa gtgcttttgt ggtagtcttg    120
tggcttccat atctggggag cttcatttgc ctttatagta ttaaccttct gagggaaaag    180
ggttgaggaa gcacccttct cttctt                                        206

<210> SEQ ID NO 22
<211> LENGTH: 11027
<212> TYPE: DNA
<213> ORGANISM: artificial
<220> FEATURE:
<223> OTHER INFORMATION: GM-159-FAD2-1b(22)/KS322 plasmid
<220> FEATURE:
<221> NAME/KEY: misc_feature
<222> LOCATION: (2349)..(2349)
<223> OTHER INFORMATION: n is a, c, g, or t

<400> SEQUENCE: 22
ggccgcaagt atgaactaaa atgcatgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta accttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatatttag ttgatatgta    540 tatgaaaggg tactatttga actctcttac tctgtataaa ggttggatca tccttaaagt    600
```

```
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaattttta atttgagttg tcttgtttgc   1020
tgcataattt atgcagtaaa acactacaca taacccttt agcagtagag caatggttga   1080
ccgtgtgctt agcttctttt atttattt tttatcagca aagaataaat aaaataaaat   1140
gagacacttc agggatgttt caacaagctt ggatcctcga agagaagggt taataacaca   1200
cttttttaac atttttaaca caaattttag ttatttaaaa atttattaaa aaatttaaaa   1260
taagaagagg aactctttaa ataaatctaa cttacaaaat ttatgatttt taataagttt   1320
tcaccaataa aaaatgtcat aaaaatatgt taaaaagtat attatcaata ttctctttat   1380
gataaataaa aagaaaaaaa aataaaaagt taagtgaaaa tgagattgaa gtgactttag   1440
gtgtgtataa atatatcaac cccgccaaca atttatttaa tccaaatata ttgaagtata   1500
ttattccata gcctttattt atttatatat ttattatata aaagctttat ttgttctagg   1560
ttgttcatga aatattttt tggttttatc tccgttgtaa gaaaatcatg tgctttgtgt   1620
cgccactcac tattgcagct ttttcatgca ttggtcagat tgacggttga ttgtattttt   1680
gttttttatg gttttgtgtt atgacttaag tcttcatctc tttatctctt catcaggttt   1740
gatggttacc taatatggtc catgggtaca tgcatggtta aattaggtgg ccaactttgt   1800
tgtgaacgat agaattttt ttatattaag taaactattt ttatattatg aaataataat   1860
aaaaaaaata ttttatcatt attaacaaaa tcatattagt taatttgtta actctataat   1920
aaaagaaata ctgtaacatt cacattacat ggtaacatct ttccacccctt tcatttgttt   1980 tttgtttgat gactttttt cttgtttaaa tttatttccc ttcttttaaa tttggaatac   2040
attatcatca tatataaact aaaatactaa aaacaggatt acacaaatga taaataataa   2100
cacaaatatt tataaatcta gctgcaatat atttaaacta gctatatcga tattgtaaaa   2160
taaaactagc tgcattgata ctgataaaaa aatatcatgt gctttctgga ctgatgatgc   2220
agtatacttt tgacattgcc tttatttat ttttcagaaa agctttctta gttctgggtt   2280
cttcattatt tgtttcccat ctccattgtg aattgaatca tttgcttcgt gtcacaaata   2340
caatttagnt aggtacatgc attggtcaga ttcacggttt attatgtcat gacttaagtt   2400
catggtagta cattacctgc cacgcatgca ttatattggt tagatttgat aggcaaatt   2460 ggttgtcaac aatataaata taaataatgt ttttatatta cgaaataaca gtgatcaaaa   2520
caaacagttt tatctttatt aacaagattt tgttttgtt tgatgacgtt ttaatgtt   2580 tacgctttcc cccttctttt gaatttagaa cactttatca tcataaaatc aaatactaaa   2640 aaattacat atttcataaa taataacaca atatttta aaaatctga aataataatg   2700 aacaatatta catattatca cgaaaattca ttaataaaaa tattatataa ataaaatgta   2760
atagtagtta tatgtaggaa aaaagtactg cacgcataat atatacaaaa agattaaaat   2820
gaactattat aaataataac actaaattaa tggtgaatca tatcaaaata atgaaaaagt   2880
aaataaaatt tgtaattaac ttctatatgt attacacaca caaataataa ataatagtaa   2940
aaaaaattat gataaatatt taccatctca taagatattt aaaataatga taaaaatata   3000
```

```
gattattttt tatgcaacta gctagccaaa aagagaacac gggtatatat aaaaagagta   3060
cctttaaatt ctactgtact tcctttattc ctgacgtttt tatatcaagt ggacatacgt   3120
gaagatttta attatcagtc taaatatttc attagcactt aatactttc tgttttattc    3180 ctatcctata agtagtcccg attctcccaa cattgcttat tcacacaact aactaagaaa   3240
gtcttccata gccccccaag cggcccatgg cctcctccga ggacgtcatc aaggagttca   3300
tgcgcttcaa ggtgcgcatg gagggctccg tgaacggcca cgagttcgag atcgagggcg   3360
agggcgaggg ccgcccctac gagggcaccc agaccgccaa gctgaaggtg accaagggcg   3420
gccccctgcc cttcgcctgg gacatcctgt cccccagtt ccagtacggc tccaaggtgt    3480
acgtgaagca ccccgccgac atccccgact acaagaagct gtccttcccc gagggcttca   3540
agtgggagcg cgtgatgaac ttcgaggacg gcggcgtggt gaccgtgacc caggactcct   3600
ccctgcagga cggctccttc atctacaagg tgaagttcat cggcgtgaac ttcccctccg   3660
acggccccgt aatgcagaag aagactatgg gctgggaggc ctccaccgag cgcctgtacc   3720
cccgcgacgg cgtgctgaag ggcgagatcc acaaggccct gaagctgaag gacggcggcc   3780
actacctggt ggagttcaag tccatctaca tggccaagaa gcccgtgcag ctgcccggct   3840
actactacgt ggactccaag ctggacatca cctcccacaa cgaggactac accatcgtgg   3900
agcagtacga gcgcgccgag ggccgccacc acctgttcct gtagcggccg gccgcgacac   3960
aagtgtgaga gtactaaata aatgctttgg ttgtacgaaa tcattacact aaataaaata   4020
atcaaagctt atatatgcct tccgctaagg ccgaatgcaa agaaattggt tctttctcgt   4080
tatcttttgc cactttact agtacgtatt aattactact taatcatctt tgtttacggc     4140
tcattatatc cgtcgacggc gcgggccgct ctagaactag tggatccgtc gacggcgcgc   4200
ccgatcatcc ggatatagtt cctcctttca gcaaaaaacc cctcaagacc cgtttagagg   4260
ccccaagggg ttatgctagt tattgctcag cggtggcagc agccaactca gcttcctttc   4320
gggctttgtt agcagccgga tcgatccaag ctgtacctca ctattccttt gccctcggac   4380
gagtgctggg gcgtcggttt ccactatcgg cgagtacttc tacacagcca tcggtccaga   4440
cggccgcgct tctgcgggcg atttgtgtac gcccgacagt cccggctccg gatcggacga   4500
ttgcgtcgca tcgaccctgc gcccaagctg catcatcgaa attgccgtca accaagctct   4560
gatagagttg gtcaagacca atgcggagca tatacgcccg gagccgcggc gatcctgcaa   4620
gctccggatg cctccgctcg aagtagcgcg tctgctgctc catacaagcc aaccacggcc   4680
tccagaagaa gatgttggcg acctcgtatt gggaatcccc gaacatcgcc tcgctccagt   4740
caatgaccgc tgttatgcgg ccattgtccg tcaggacatt gttggagccg aaatccgcgt   4800
gcacgaggtg ccggacttcg gggcagtcct cggcccaaag catcagctca tcgagagcct   4860
gcgcgacgga cgcactgacg gtgtcgtcca tcacagtttg ccagtgatac acatggggat   4920
cagcaatcgc gcatatgaaa tcacgccatg tagtgtattg accgattcct tgcggtccga   4980
atgggccgaa cccgctcgtc tggctaagat cggccgcagc gatcgcatcc atagcctccg   5040
cgaccggctg cagaacagcg ggcagttcgg tttcaggcag gtcttgcaac gtgacaccct   5100
gtgcacggcg ggagatgcaa taggtcaggc tctcgctgaa ttccccaatg tcaagcactt   5160
ccggaatcgg gagcgcggcc gatgcaaagt gccgataaac ataacgatct tgtagaaac    5220 catcggcgca gctatttacc cgcaggacat atccacgccc tcctacatcg aagctgaaag   5280
cacgagattc ttcgccctcc gagagctgca tcaggtcgga gacgctgtcg aacttttcga   5340
tcagaaactt ctcgacagac gtcgcggtga gttcaggctt ttccatgggt atatctcctt   5400
```

```
cttaaagtta aacaaaatta tttctagagg gaaaccgttg tggtctccct atagtgagtc    5460
gtattaattt cgcgggatcg agatcgatcc aattccaatc ccacaaaaat ctgagcttaa    5520
cagcacagtt gctcctctca gagcagaatc gggtattcaa caccctcata tcaactacta    5580
cgttgtgtat aacggtccac atgccggtat atacgatgac tggggttgta caaaggcggc    5640
aacaaacggc gttcccggag ttgcacacaa gaaatttgcc actattacag aggcaagagc    5700
agcagctgac gcgtacacaa caagtcagca aacagacagg ttgaacttca tccccaaagg    5760
agaagctcaa ctcaagccca agagctttgc taaggcccta acaagcccac caaagcaaaa    5820
agcccactgg ctcacgctag gaaccaaaag gcccagcagt gatccagccc caaaagagat    5880 ctccttttgcc ccggagatta caatggacga tttcctctat ctttacgatc taggaaggaa    5940
gttcgaaggt gaaggtgacg acactatgtt caccactgat aatgagaagg ttagcctctt    6000
caatttcaga aagaatgctg acccacagat ggttagagag gcctacgcag caggtctcat    6060
caagacgatc tacccgagta acaatctcca ggagatcaaa taccttccca agaaggttaa    6120
agatgcagtc aaaagattca ggactaattg catcaagaac acagagaaag acatatttct    6180
caagatcaga agtactattc cagtatggac gattcaaggc ttgcttcata aaccaaggca    6240
agtaatagag attggagtct ctaaaaaggt agttcctact gaatctaagg ccatgcatgg    6300
agtctaagat tcaaatcgag gatctaacag aactcgccgt gaagactggc gaacagttca    6360
tacagagtct tttacgactc aatgacaaga agaaaatctt cgtcaacatg gtggagcacg    6420
acactctggt ctactccaaa aatgtcaaag atacagtctc agaagaccaa agggctattg    6480
agacttttca acaaaggata atttcgggaa acctcctcgg attccattgc ccagctatct    6540
gtcacttcat cgaaaggaca gtagaaaagg aaggtggctc ctacaaatgc catcattgcg    6600
ataaaggaaa ggctatcatt caagatgcct ctgccgacag tggtcccaaa gatgaccccc    6660
cacccacgag gagcatcgtg gaaaaagaag acgttccaac cacgtcttca agcaagtgg    6720 attgatgtga catctccact gacgtaaggg atgacgcaca atcccactat ccttcgcaag    6780
acccttcctc tatataagga agttcatttc atttggagag gacacgctcg agctcatttc    6840
tctattactt cagccataac aaaagaactc ttttctcttc ttattaaacc atgaaaaagc    6900
ctgaactcac cgcgacgtct gtcgagaagt ttctgatcga aaagttcgac agcgtctccg    6960
acctgatgca gctctcggag gcgaagaat ctcgtgcttt cagcttcgat gtaggagggc    7020
gtggatatgt cctgcgggta aatagctgcg ccgatggttt ctacaaagat cgttatgttt    7080
atcggcactt tgcatcggcc gcgctcccga ttccggaagt gcttgacatt ggggaattca    7140
gcgagagcct gacctattgc atctcccgcc gtgcacaggg tgtcacgttg caagacctgc    7200
ctgaaaccga actgcccgct gttctgcagc cggtcgcgga ggccatggat gcgatcgctg    7260
cggccgatct tagccagacg agcgggttcg gcccattcgg accgcaagga atcggtcaat    7320
acactacatg gcgtgatttc atatgcgcga ttgctgatcc ccatgtgtat cactggcaaa    7380
ctgtgatgga cgacaccgtc agtgcgtccg tcgcgcaggc tctcgatgag ctgatgcttt    7440
gggccgagga ctgccccgaa gtccggcacc tcgtgcacgc ggatttcggc tccaacaatg    7500
tcctgacgga caatggccgc ataacagcgg tcattgactg gagcgaggcg atgttcgggg    7560
attcccaata cgaggtcgcc aacatcttct tctggaggcc gtggttggct tgtatggagc    7620
agcagacgcg ctacttcgag cggaggcatc cggagcttgc aggatcgccg cggctccggg    7680
cgtatatgct ccgcattggt cttgaccaac tctatcagag cttggttgac ggcaatttcg    7740
atgatgcagc ttgggcgcag ggtcgatgcg acgcaatcgt ccgatccgga gccgggactg    7800
```

-continued

| | |
|---|---|
| tcgggcgtac acaaatcgcc cgcagaagcg cggccgtctg gaccgatggc tgtgtagaag | 7860 |
| tactcgccga tagtggaaac cgacgcccca gcactcgtcc gagggcaaag gaatagtgag | 7920 |
| gtacctaaag aaggagtgcg tcgaagcaga tcgttcaaac atttggcaat aaagtttctt | 7980 |
| aagattgaat cctgttgccg gtcttgcgat gattatcata taatttctgt tgaattacgt | 8040 |
| taagcatgta ataattaaca tgtaatgcat gacgttattt atgagatggg tttttatgat | 8100 |
| tagagtcccg caattataca tttaatacgc gatagaaaac aaaatatagc gcgcaaacta | 8160 |
| ggataaatta tcgcgcgcgg tgtcatctat gttactagat cgatgtcgaa tctgatcaac | 8220 |
| ctgcattaat gaatcggcca acgcgcgggg agaggcggtt tgcgtattgg gcgctcttcc | 8280 |
| gcttcctcgc tcactgactc gctgcgctcg tcgttcggc tgcggcgagc ggtatcagct | 8340 |
| cactcaaagg cggtaatacg gttatccaca gaatcagggg ataacgcagg aaagaacatg | 8400 |
| tgagcaaaag gccagcaaaa ggccaggaac cgtaaaaagg ccgcgttgct ggcgtttttc | 8460 |
| cataggctcc gccccctga cgagcatcac aaaaatcgac gctcaagtca gaggtggcga | 8520 |
| aacccgacag gactataaag ataccaggcg tttccccctg gaagctccct cgtgcgctct | 8580 |
| cctgttccga ccctgccgct taccggatac ctgtccgcct ttctcccttc gggaagcgtg | 8640 |
| gcgctttctc aatgctcacg ctgtaggtat ctcagttcgg tgtaggtcgt tcgctccaag | 8700 |
| ctgggctgtg tgcacgaacc ccccgttcag cccgaccgct gcgccttatc cggtaactat | 8760 |
| cgtcttgagt ccaacccggt aagacacgac ttatcgccac tggcagcagc cactggtaac | 8820 |
| aggattagca gagcgaggta tgtaggcggt gctacagagt tcttgaagtg gtggcctaac | 8880 |
| tacggctaca ctagaaggac agtatttggt atctgcgctc tgctgaagcc agttaccttc | 8940 |
| ggaaaaagag ttggtagctc ttgatccggc aaacaaacca ccgctggtag cggtggtttt | 9000 |
| tttgtttgca agcagcagat tacgcgcaga aaaaaaggat ctcaagaaga tcctttgatc | 9060 |
| ttttctacgg ggtctgacgc tcagtggaac gaaaactcac gttaagggat tttggtcatg | 9120 |
| acattaacct ataaaaatag gcgtatcacg aggccctttc gtctcgcgcg tttcggtgat | 9180 |
| gacggtgaaa acctctgaca catgcagctc ccggagacgg tcacagcttg tctgtaagcg | 9240 |
| gatgccggga gcagacaagc ccgtcagggc gcgtcagcgg gtgttggcgg gtgtcggggc | 9300 |
| tggcttaact atgcggcatc agagcagatt gtactgagag tgcaccatat ggacatattg | 9360 |
| tcgttagaac gcggctacaa ttaatacata accttatgta tcatacacat acgatttagg | 9420 |
| tgacactata gaacggcgcg ccaagctttt gatccatgcc cttcatttgc cgcttattaa | 9480 |
| ttaatttggt aacagtccgt actaatcagt tacttatcct tccccatca taattaatct | 9540 |
| tggtagtctc gaatgccaca acactgacta gtctcttgga tcataagaaa aagccaagga | 9600 |
| acaaagaag acaaaacaca atgagagtat cctttgcata gcaatgtcta agttcataaa | 9660 |
| attcaaacaa aaacgcaatc acacacagtg gacatcactt atccactagc tgatcaggat | 9720 |
| cgccgcgtca agaaaaaaaa actgaccccc aaaagccatg cacaacaaca cgtactcaca | 9780 |
| aaggtgtcaa tcgagcagcc caaaacattc accaactcaa cccatcatga gccctcacat | 9840 |
| ttgttgtttc taacccaacc tcaaactcgt attctcttcc gccacctcat ttttgtttat | 9900 |
| tcaacacccc gtcaaactgc atgccacccc gtggccaaat gtccatgcat gttaacaaga | 9960 |
| cctatgacta taaatagctg caatctcggc ccaggttttc atcatcaaga accagttcaa | 10020 |
| tatcctagta caccgtatta aagaatttaa gatatactgc ggccgcttct agctagctag | 10080 |
| ggtttgggta gtgagtgtaa taaagttgca agttttttgg ttaggttacg ttttgacctt | 10140 |
| attattatag ttcaaaggga aacattaatt aaagggggatt atgaagcttc ccaacccaat | 10200 |

-continued

```
tccctcttga ggatcttact gggtgaattg agctgcttag ctatggatcc cacagttcta    10260
cccatcaata agtgcttttg tggtagtctt gtggcttcca tatctgggga gcttcatttg    10320
cctttatagt attaaccttc tgagggaaaa gggttgagga agcacccttc tcttcttttc    10380
tctcataata atttaaattt gttatagact ctaaacttta aatgtttttt ttgaagtttt    10440
tccgtttttc tcttttgcca tgatcccgtt cttgctgtgg agtaaccttg tccgaggtat    10500
gtgcatgatt agatccatac ttaatttgtg tgcatcacga aggtgaggtt gaaatgaact    10560 ttgcttttttt gaccttttag gaaagttctt ttgttgcagt aatcaatttt aattagtttt    10620
aattgacact attacttttta ttgtcatctt tgttagtttt attgttgaat tgagtgcata    10680
tttcctagga aattctctta cctaacattt tttatacaga tctatgctct tggctcttgc    10740
ccttactctt ggccttgtgt tggttatttg tctacatatt tattgactgg tcgatgagac    10800
atgtcacaat tcttgggctt atttgttggt ctaataaaag gagtgcttat tgaaagatca    10860
agacggagat tcggttttat ataaataaac taaagatgac atattagtgt gttgatgtct    10920
cttcaggata atttttgttt gaaataatat ggtaatgtct tgtctaaatt tgtgtacata    10980
attcttactg attttttgga ttgttggatt tttataaaca aatctgc                  11027
```